(12) United States Patent
Shen et al.

(10) Patent No.: US 8,188,032 B2
(45) Date of Patent: May 29, 2012

(54) G-CSF TRANSFERRIN FUSION PROTEINS

(75) Inventors: Wei-Chiang Shen, San Marino, CA (US); Yun Bai, Tucker, GA (US); David Ann, Arcadia, CA (US); Adam Widera, Long Beach, CA (US)

(73) Assignee: National Institutes of Health (NIH), Bethesda, MD (US)

( * ) Notice: Subject to any disclaimer, the term of this patent is extended or adjusted under 35 U.S.C. 154(b) by 331 days.

(21) Appl. No.: 10/575,033

(22) PCT Filed: Oct. 8, 2004

(86) PCT No.: PCT/US2004/033337
§ 371 (c)(1),
(2), (4) Date: Jan. 8, 2008

(87) PCT Pub. No.: WO2005/034877
PCT Pub. Date: Apr. 21, 2005

(65) Prior Publication Data
US 2009/0042777 A1     Feb. 12, 2009

Related U.S. Application Data

(60) Provisional application No. 60/510,652, filed on Oct. 10, 2003, provisional application No. 60/577,150, filed on Jun. 4, 2004.

(51) Int. Cl.
*A61K 38/00* (2006.01)
*A61P 7/06* (2006.01)
(52) U.S. Cl. ............... 514/1.1; 514/7.9; 530/350
(58) Field of Classification Search ............ None
See application file for complete search history.

(56) References Cited

U.S. PATENT DOCUMENTS

| 5,254,342 | A | | 10/1993 | Shen et al. ............... 424/401 |
| 5,665,863 | A | * | 9/1997 | Yeh ............... 530/351 |
| 5,672,683 | A | * | 9/1997 | Friden et al. ............... 530/350 |
| 7,176,278 | B2 | * | 2/2007 | Prior ............... 530/308 |
| 2003/0082679 | A1 | | 5/2003 | Sun et al. |
| 2003/0144198 | A1 | | 7/2003 | Collins |

FOREIGN PATENT DOCUMENTS

WO    WO 93/20834    10/1993

OTHER PUBLICATIONS

Widera et al., Pharm. Res. vol. 20: 1231-1238, 2003.*
Mouz et al., Nutrition 16: 229-230, 2000.*
Deven Shah, et al. "Transcellular Delivery of an Insulin-Transferrin Conjugate in Enterocyte-like Caco-2 Cells" (Journal of Pharmaceutical Sciences, American Pharmaceutical Assoc., Washington, US, vol. 85, No. 12, Dec. 1996, pp. 1306-1311, XP002906594, ISSN: 0022-3549).
Deven Shah, et al. "The Establishment of Polarity and Enhanced Transcytosis of Transferrin Receptors in Enterocyte-like Caco-2 Cells" (Journal of Drug Targeting, vol. 2, No. 2, 1994, pp. 93-99; XP-009094607, Switzerland).
Wendy Halpern, et al. "Albugranin™, a Recombinant Human Granulocyte Colony Stimulating Factor (G-CSF) Genetically Fused to Recombinant Human Albumin Induces Prolonged Myelopoietic Effects in Mice and Monkeys" (Pharmaceutical Research Nov. 2002, vol. 19, No. 11, Nov. 2002, pp. 1720-1729; XP-002464933; ISSN: 0724-8741).
Ophry Pines, et al. "Expression and Secretion of Proteins in *E. coli*" (Molecular Biotechnology, Totowa, NJ, US, vol. 2, No. 1, 1999, pp. 25-34; XP-000985935; ISSN:1073-6085).
G.E. Grampp, et al. "Use of Regulated Secretion in Protein Production From Animal Cells: An Overview" (Advances in Biochemical Engineering/Biotechnology 1992, vol. 46, 1992, pp. 35-62; XP-009094668; ISSN: 0724-6145).
Lynn McCarroll, et al. "Stable insect cell cultures for recombinant protein production" (Current Opinion in Biotechnology Oct. 1997, vol. 8, No. 5, Oct. 1997, pp. 590-594; XP-002464935; ISSN: 0958-1669).
Richard G. Buckholz, et al. "Yeast Systems for the Commercial Production of Heterologous Proteins" (Bio/Technology, Nature Publishing Co. New York, US, vol. 9, Nov. 1991, pp. 1067-1072; XP-000918924; ISSN: 0733-222X).
S. Hohaus, et al. "Recombinant human granulocyte and granulocyte-macrophage colony-stimulating factor (G-CSF and GM-CSF) administered following cytotoxic chemotherapy have a similar ability to mobilize peripheral blood stems cells" Bone Marrow Transplantation Oct. 1998, vol. 22, No. 7, Oct. 1998, pp. 625-630; XP-002464936 ISSN: 0268-3369).
Mutay Asian, et al. "The effect of recombinant human granulocyte/macrophage-colony-stimulating factor (rHu GM-CSF) and rHu G-CSF administration on neutrophil chemiluminescence assay in patients following cyclic chemotheraphy" (Cancer Immunology, Immunotherapy : CII Nov. 1998, vol. 47, No. 3, pp. 176-181; XP 002464937 ISSN: 0340-7004).
Adam Widera, et al. "The Transepithelial Transport of a G-CSF-Transferrin Conjugate in Caco-2 Cells and Its Myelopoietic Effect in BDF1 Mice" (Pharmaceutical Research Feb. 2004, vol. 21, No. 2, pp. 278-284; XP-002464938; ISSN: 0724-8741).
PCT Search Report for corresponding PCT application No. PCT/US04/33337 lists the references above.

\* cited by examiner

*Primary Examiner* — Gyan Chandra
(74) *Attorney, Agent, or Firm* — DLA Piper LLP (US)

(57) ABSTRACT

A polypeptide comprising a G-CSF domain operably linked to a Tf domain, wherein the ability of the polypeptide to be transported into a cell expressing a TfR gene or the ability of the polypeptide to be transported across a cell expressing a TfR gene via transcytosis is higher than that of the G-CSF domain alone.

11 Claims, 11 Drawing Sheets

(a)

(b)

G-CSF TRANSFERRIN FUSION PROTEINS

RELATED APPLICATIONS

This application claims priority to U.S. Provisional Application Ser. No. 60/510,652, filed Oct. 10, 2003, and U.S. Provisional Application Ser. No. 60/577,150, filed Jun. 4, 2004, the contents of which are incorporated herein by reference in their entirety.

This invention was made with support in part by NIH grant R01 GM63647. Therefore, the U.S. government has certain rights.

FIELD OF THE INVENTION

The present invention relates to granulocyte colony stimulating factor (G-CSF)-transferrin (Tf) fusion proteins (e.g., conjugate and recombinant proteins) that can be used for treating various diseases such as immune deficient diseases in a subject. More specifically, the invention relates to oral or subcutaneous administration of G-CSF-Tf fusion proteins to a subject in need thereof.

BACKGROUND OF THE INVENTION

Filgrastim (recombinant metHu G-CSF) is indicated in clinical conditions where it is desired to have increased production of circulating neutrophils. Common clinical indications include, severe chronic neutropenia, bone marrow transplants, and patients undergoing chemotherapy for various cancers. One of the drawbacks of the current filgrastim therapy protocol is the need for daily or twice-daily injections. This comes as a result of the short half-life of the drug of only several hours (1).

Recently several drugs have been developed that have sought to address the short half-life of filgrastim. For example, these have included pegylation of G-CSF (2) and the creation of G-CSF-albumin fusion constructs (3). Reduced clearance rates of the protein-drug have been reported for these modifications to G-CSF. However, these alterations to standard filgrastim dosing regimes are still limited to invasive administration.

The current subcutaneous filgrastim dosing regime is less than ideal for the patient because of the inconvenience and pain brought about by repeated injections. Non-invasive delivery methods have been a subject of interest for protein-based therapeutics as an alternative to the current subcutaneous or IV dosing. Nasal (4), rectal (5), pulmonary (6):361-373), ocular (7), and oral administration routes are among those that have been investigated. Among all of these, oral is the most preferred because it requires no specialized delivery device and it is most convenient for the patient. However, oral delivery of protein-drugs is hampered by negligible bioavailability. Protein based drugs are hampered by instability and proteolysis in the gastro-intestinal tract. The large size and charged nature of the molecules also prevents them from traversing biological barriers. Co-administration and/or formulation with penetration enhancers and enzymatic inhibitors has been suggested as a means to achieve oral bioavailability of protein-drugs (8; 9). However, the suitability of these methods for chronic usage remains questionable as they have been shown to be associated with adverse side-effects (10-12). Development of new dosing regimes is needed.

SUMMARY OF THE INVENTION

The present invention relates to a novel G-CSF-Tf fusion protein that can be used for treating various diseases in a subject.

In one aspect, the invention features a polypeptide comprising a G-CSF domain operably linked to a Tf domain. The ability of the polypeptide to be transported into a cell expressing a transferring receptor (TfR) gene or the ability of the polypeptide to be transported across a cell expressing a TfR gene via transcytosis is higher than that of the G-CSF domain alone. The G-CSF domain and the Tf domain may be linked through non-covalent or covalent bonding. For example, the G-CSF domain and the Tf domain may be linked through a disulfide bond. In another example, the polypeptide is a recombinant polypeptide. The G-CSF domain may be linked to the Tf domain through a linker (e.g., a Leu-Glu linker) in the recombinant polypeptide. The recombinant polypeptide may also have a secretion signal at the N-terminus to facilitate secretion of the polypeptide from a cell. The order of the G-CSF domain and the Tf domain may be from the N-terminus to the C-terminus in the recombinant polypeptide. In some embodiments, the Tf domain comprises at least one (e.g., two) iron molecule.

In another aspect, the invention features a nucleic acid comprising a DNA sequence encoding a polypeptide of the invention, as well as a cell harboring such a nucleic acid. The nucleic acid and the cell can be used for production of the polypeptide.

The invention further provides a composition comprising a pharmaceutically acceptable carrier and a polypeptide or the nucleic acid of the invention. Such a composition can be used for treating various diseases in a subject. When a polypeptide composition is delivered, the composition may include agents (e.g., sodium bicarbonate, BSA or casein) to help increase the stability of the polypeptide.

Also within the scope of the invention is a method of producing a polypeptide by cultivating a cell of the invention under conditions that allow expression of the polypeptide of the invention. The polynucleotide can then be collected.

The invention further provides a method of enhancing transport of G-CSF into or across a gastrointestinal (GI) epithelial cell. The method involves contacting a GI epithelial cell with a polypeptide of the invention under conditions that allow transport of the polypeptide into the cell through TfR or transport of the polypeptide across the cell through TfR via transcytosis.

Moreover, the invention provides a method of enhancing transport of a polypeptide into or across a GI epithelial cell. The method involves contacting a GI epithelial cell with a polypeptide operably linked to a Tf domain under conditions that allow transport of the Tf-linked polypeptide into the cell through TfR or transport of the Tf-linked polypeptide across the cell through TfR via transcytosis. The molecular weight of the polypeptide is at least 10 kD (e.g., 15 kD or 20 kD), the size of the Tf-linked polypeptide is no more than 200 nm, and the ability of the Tf-linked polypeptide to be transported into a cell expressing a TfR gene or the ability of the Tf-linked polypeptide to be transported across a cell expressing a TfR gene via transcytosis is higher than that of the polypeptide alone.

Also within the scope of the invention is a method of enhancing transport of a polypeptide; into or across a GI epithelial cell, comprising contacting a GI epithelial cell with a recombinant protein containing a polypeptide operably linked to a Tf domain under conditions that allow transport of the Tf-linked polypeptide into the cell through TfR or transport of the Tf-linked polypeptide across the cell through TfR via transcytosis. The ability of the Tf-linked polypeptide, to be transported into a cell expressing a TfR gene or the ability of the Tf-linked polypeptide to be transported across a cell expressing a TfR gene via transcytosis is higher than that of the polypeptide alone. The polypeptide may include, e.g., a G-CSF domain.

In addition, the invention provides a method of enhancing production of circulating neutrophils in a subject (e.g., a mammal such as a human). The method involves administering to a subject in need thereof an effective amount of a composition of the invention. The subject may be undergoing chemotherapy for cancer, or is suffering from or at risk for developing severe chronic neutropenia or a bone marrow transplant-related disorder. The composition is administered orally or subcutaneously.

Unless otherwise defined, all technical and scientific terms used herein have the same meaning as commonly understood by one of ordinary skill in the art to which this invention pertains. In case of conflict, the present document, including definitions, will control. All publications, patent applications, patents and other references mentioned herein are incorporated by reference in their entirety. The materials, methods, and examples disclosed herein are illustrative only and not intended to be limiting. Other features, objects, and advantages of the invention will be apparent from the description and the accompanying drawings, and from the claims.

DETAILED DESCRIPTION OF THE INVENTION

Figure 1:
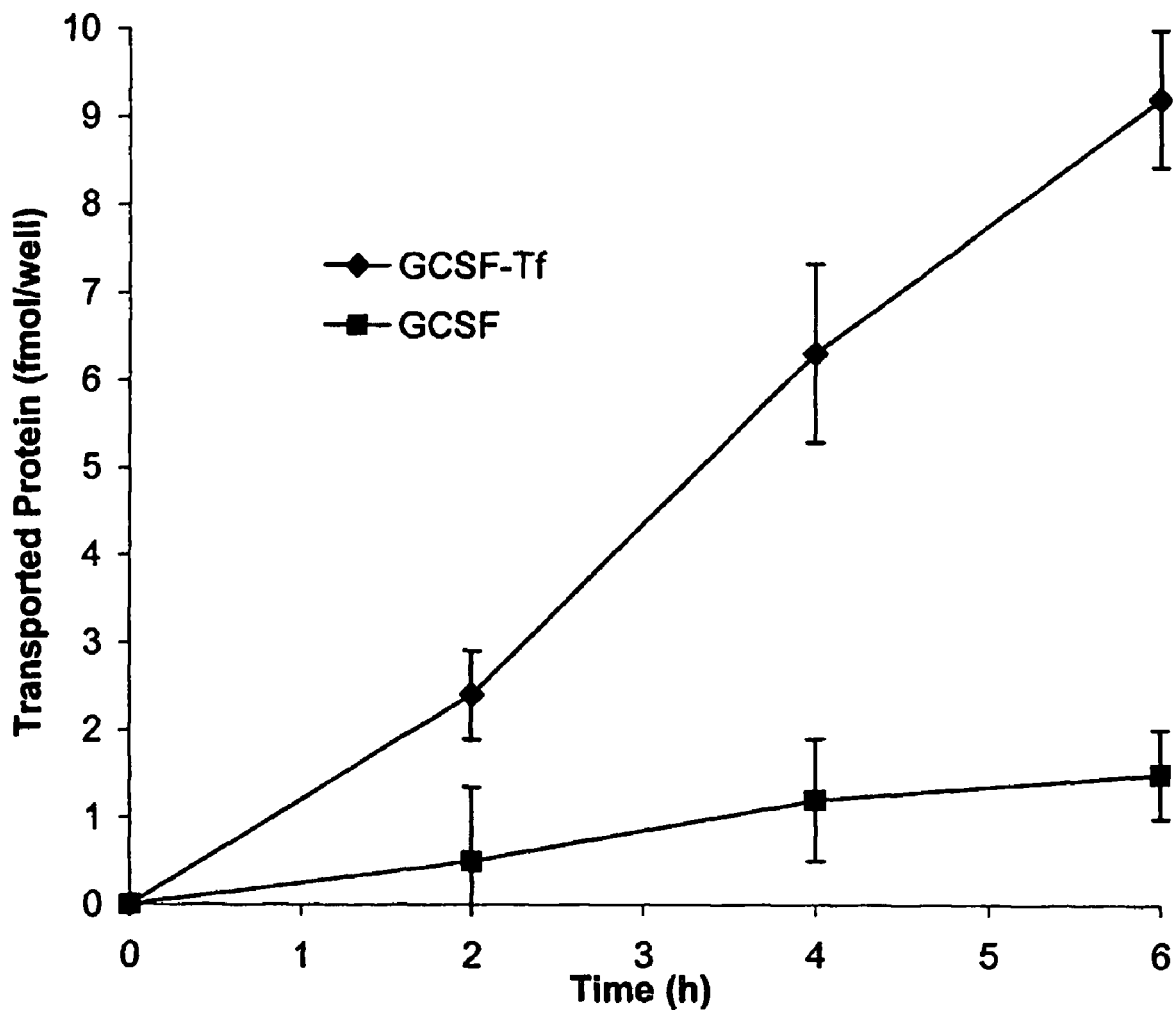
FIG. 1 illustrates specific TfR-mediated transport of $^{125}$I-G-CSF-transferrin conjugate determined in Caco-2 monolayers and comparison to $^{125}$I-G-CSF. The apical compartments of two week-old Caco-2 monolayers were dosed with 1.5 μg/mL of $^{125}$I-G-CSF-Tf or $^{125}$I-G-CSF. Samples were taken from the basolateral compartments at regular intervals, subjected to 15% TCA precipitation, and radioactivity counted on a Packard gamma counter. Non-specific $^{125}$I-Tf transport was determined in parallel by the inclusion of 10-fold molar excess of non-radiolabeled Tf. The apical-to-basolateral transport of $^{125}$I-G-CSF was not affected by the presence of excess Tf while $^{125}$I-G-CSF-Tf exhibited a 80% reduction in transport (n=3).

Natural transcytotic pathways, such as the TfR, are utilized to enable the transepithelial and transendothelial delivery of large protein-based therapeutic molecules in the present invention. Transcytosis of TfR does not alter cellular processes and would conceivably be less detrimental to membrane integrity than other methods that enable transport of protein-drugs. TfR is also a good candidate for targeting within the gastrointestinal tract since TfR has been reported to be highly expressed in the human GI epithelium. Transferrin (Tf) is also resistant to chymotryptic and tryptic digestion, two common proteolytic outcomes encountered by orally delivered protein-drugs. In addition, Tf is naturally released by the pancreas as part of normal digestive processes. This release of Tf by the pancreas is thought to facilitate the partial uptake of iron and regulation of iron homeostasis through the small intestine epithelium (13-15), thus providing a potential route of uptake for TfR targeted protein-drug-Tf conjugates.

The present invention is based, in part, on the unexpected discovery that a G-CSF-Tf fusion protein exhibits an increased duration of neutrophil proliferation action in mice (compared to filgrastim) with the added benefit of oral bioavailability. As the mouse model has consistently predicted the biochemistry and outcome in other animals and in human, the G-CSF-Tf fusion protein may be used for treating other animals and human as well. The fusion protein described here enables the production of a large quantity of a pure protein drug for the treatment of immune deficiency due to genetic abnormality in granulocyte proliferation or to the myelotoxicity of cancer chemotherapeutic drugs.

Polypeptides

A polypeptide of the invention (i.e., a G-CSF-Tf fusion protein) comprises a G-CSF domain and a Tf domain operably linked to each other. "G-CSF-Tf fusion protein" refers to a composite protein containing both a G-CSF domain and a Tf domain.

A "G-CSF domain" is a protein domain that retains the biological functions of G-CSF, i.e., promoting the proliferation, survival, maturation and functional activation of cells from the neutrophilic granulocyte lineage. In one embodiment, the G-CSF domain may have the wild-type amino acid sequence of a G-CSF protein (e.g., a human G-CSF protein). In other embodiments, the G-CSF domain may be a variant of the wild-type G-CSF. G-CSF variants may be constructed by, for example, substituting or deleting residues not needed for G-CSF's biological functions or by inserting residues that will not affect G-CSF's biological functions. Generally, substitutions should be made conservatively, i.e., the most preferred substitute amino acids are those having physiochemical characteristics resembling those of the residues to be replaced. Examples of conservative substitutions include substitution of one aliphatic residue for another, such as Ile, Val, Leu, or Ala for one another, or substitution of one polar residue for another, such as between Lys and Arg, Glu and Asp, or Gln and Asn. Other such conservative substitutions, for example, substitution of an entire region with another having similar hydrophobicity characteristics, are well known in the art. Moreover, particular amino acid differences between human, murine and other mammalian G-CSFs are suggestive of additional conservative substitutions that may be made without altering the essential biological characteristics of the G-CSF protein. The activity of a G-CSF domain may be determined using any of the methods known in the art. For example, a NFS-60 MTT proliferation assay may be employed as described in Example 1 below.

A "Tf domain" is a protein domain that retains the biological functions of Tf, i.e., binding and transporting iron. In one embodiment, the Tf domain may have the wild-type amino acid sequence of a Tf protein (e.g., a human Tf protein). In other embodiments, the Tf domain may be a variant of the wild-type Tf. Tf variants may be constructed using methods similar to those discussed above for G-CSF variants. The activity of a Tf domain may be determined using any of the methods known in the art. For example, the activity of a Tf domain may be determined by measuring its ability to bind a TfR. See Example 2 below.

The G-CSF domain and the Tf domain are operably linked in a polypeptide of the invention. As used herein, "operably linked" refers to the structural configuration of the polypeptide that does not interfere with or abolish the biological functions of each domain, i.e., the G-CSF domain remains capable of promoting the proliferation, survival, maturation and functional activation of cells from the neutrophilic granulocyte lineage, and the Tf domain remains capable of binding and transporting iron.

The G-CSF domain and the Tf domain can be physically or chemically linked. For example, the two domains may be linked through non-covalent bonding. In one embodiment, avidin may be attached to one of the domains and biotin to the other. In forming a fusion protein, the two domains are linked through avidin-biotin bridge. Alternatively, the two domains may be linked through covalent bonding. For example, cross-linking reagents may be used to generate a G-CSF-Tf fusion protein, e.g., as described in Example 1 below.

The fusion protein may also be produced as a recombinant protein. In this case, a DNA encoding the fusion protein is constructed and transcribed into an mRNA. The mRNA is then translated into the fusion protein. In the recombinant protein, the G-CSF domain and the Tf domain may be linked through a linker sequence (e.g., a Leu-Glu linker described in Example 2 below). Also, to facilitate production of the recombinant protein, a secretion signal may be added at the N-terminus of the protein. The recombinant protein will then be secreted from a cell into the culture medium and can be collected accordingly. The order of the G-CSF domain and the Tf domain in the recombinant protein may vary. In one embodiment, the G-CSF domain is located to N-terminus of the Tf domain. In another embodiment, the G-CSF domain is located to C-terminus of the Tf domain.

In some embodiments, the Tf domain may be preloaded with at least one (e.g., two or three) iron molecule. When the fusion protein is produced as a recombinant protein, the Tf domain may pick up iron molecules in the medium.

When linked to a Tf domain, the G-CSF domain is transported into and across a cell through the TfR pathway. It is more efficient than transport of a G-CSF protein by itself, i.e., the ability of the G-CSF-Tf fusion protein to be transported into a cell expressing a TfR gene or the ability of the polypeptide to be transported across a cell expressing a TfR gene via transcytosis is higher than that of the G-CSF domain alone. Transcytosis is the uptake of material at one face of a cell by endocytosis, its transfer across a cell in vesicles, and its discharge from another face by exocytosis (Alberts et. al. (2002) Molecular Biology of the Cell, 4$^{th}$ edition, Garland Science, p. G-35). Transport and transcytosis of the fusion protein and the G-CSF domain may be measured and compared using any of the methods known in the art. See, e.g., Example 1, Assessment of Apical-to-Basolateral Transcytosis of $^{125}$I-Tf, $^{125}$I-G-CSF and $^{125}$I-G-CSF-Tf across Caco-2 Cell Monolayers below. If the amount of the fusion protein being transported into or across a cell is larger than that for the G-CSF domain alone, it indicates that the ability of the fusion protein being transported into or across a cell is higher than that of the G-CSF domain alone.

Also within the scope of the invention is a recombinant protein containing a polypeptide operably linked to a Tf domain. The ability of the Tf-linked polypeptide to be transported into a cell expressing a TER gene or the ability of the Tf-linked polypeptide to be transported across a cell expressing a TfR gene via transcytosis is higher than that of the polypeptide alone. The polypeptide may include, e.g. an insulin domain, growth hormone domain, erythropoietin domain, interferon (e.g., IFN-α) domain, interleukin (e.g., IL-2) domain, and immunoglobulin or its fragment (e.g., Fab and sFv) domain.

As used herein, a "domain" refers to a wild-type protein of interest, or a variant of the protein that retains the biological functions of the wild-type protein. Variants of a protein of interest may be produced using methods similar to those described above for G-CSF variants.

Nucleic Acids

The invention also provides a nucleic acid containing a DNA sequence encoding a polypeptide of the invention. Such a nucleic acid may be constructed using recombinant DNA technology well known in the art.

For example, a nucleic acid of the invention may be a vector containing a DNA sequence encoding a polypeptide of the invention. The vector can be used for production of the polypeptide. As used herein, the term "vector" refers to a nucleic acid capable of transporting another nucleic acid to which it has been linked. Various types of vectors are well known in the art. See, e.g., U.S. Pat. Nos. 6,756,196 and 6,787,345. One type of vector is a "plasmid," which refers to a circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain expression vectors are capable of directing the expression of genes to which they are operatively linked.

The recombinant expression vectors are suitable for expression of the polypeptide of the invention in a host cell. These vectors include one or more regulatory sequences, selected on the basis of the host cells, operatively linked to a nucleic acid sequence encoding the polypeptide of the invention. Within a recombinant expression vector, "operatively linked" means that the nucleic acid sequence of interest is linked to the regulatory sequences manner which allows for expression of the nucleic acid sequence (e.g., in an in vitro transcription/translation system or in a host cell when the vector is introduced into the host cell). "Regulatory sequences" refers to promoters, enhancers and other expression control elements (e.g., polyadenylation signals). Such regulatory sequences are described, for example, in Goeddel, supra. Regulatory sequences include those which direct constitutive expression of a nucleic acid sequence in many types of host cell and those which direct expression of a nucleic acid sequence only in certain host cells (e.g., tissue-specific regulatory sequences). It will be appreciated by those skilled in the art that the design of the expression vector can depend on such factors as the choice of the host cell to be transformed, the level of expression of protein desired, etc. The expression vectors can be introduced into host cells to thereby produce the polypeptide of the invention. They can be designed for expression of the polypeptide in prokaryotic or eukaryotic cells, e.g., bacterial cells such as *E. coli*, insect cells (using baculovirus expression vectors), yeast cells, or mammalian cells. Suitable host cells are discussed further in Goeddel, Gene Expression Technology Methods in Enzymology 185, Academic Press, San Diego, Calif. (1990). Alternatively, the recombinant expression vector can be transcribed and translated in vitro, for example, using T7 promoter regulatory sequences and T7 polymerase.

In one embodiment, a polypeptide of the invention is expressed in mammalian cells using a mammalian expression vector. Examples of mammalian expression vectors include pCDM8 (Seed (1987) Nature 329:840), pCI (Promega), and pMT2PC (Kaufman et al. (1987) EMBO J. 6:187-195). When used in mammalian cells, the expression vector's control functions are often provided by viral regulatory elements. For example, commonly used promoters are derived from polyoma, adenovirus 2, cytomegalovirus and Simian Virus 40. For other suitable expression systems for both prokaryotic and eukaryotic cells, see Chapters 16 and 17 of Sambrook et al. eds., Molecular Cloning: A Laboratory Manual. 2nd, ed., Cold Spring. Harbor Laboratory, Cold Spring Harbor Laboratory Press, Cold Spring Harbor, N.Y., 1989.

In another embodiment, the recombinant mammalian expression vector is capable of directing, expression of the polypeptide preferentially in a particular cell type (e.g., tissue-specific regulatory elements are used to express the polypeptide). Tissue-specific regulatory elements are known in the art. Non-limiting examples of suitable tissue-specific promoters include the albumin promoter (liver-specific; Pinkert et al. (1987) Genes Dev. 1:268-277), lymphoid-specific promoters (Calame and Eaton (1988) Adv. Immunol. 43:235-275), in particular promoters of T cell receptors (Winoto and Baltimore (1989) EMBO J. 8:729-733) and immunoglobulins (Banerji et al. (1983) Cell 33:729-740 and Queen and Baltimore (1983) Cell 33:741-748), neuron-specific promoters (e.g., the neurofilament promoter; Byrne and Ruddle (1989) Proc. Natl. Acad. Sci. USA 86:5473-5477), pancreas-specific promoters (Edlund et al. (1985) Science 230:912-916), and mammary gland-specific promoters (e.g., milk whey promoter; U.S. Pat. No. 4,873,316 and European Application Publication No. 264,166). Developmentally-regulated promoters are also encompassed, for example the murine hox promoters (Kessel and Gruss (1990) Science 249:374-379) and the alpha-fetoprotein promoter (Campes and Tilghman (1989) Genes Dev. 3:537-546).

Cells

Another aspect of the invention pertains to host cells into which a nucleic acid of the invention has been introduced. The terms "host cell" refers not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

A host cell can be any prokaryotic or eukaryotic cell. For example, a polypeptide of the invention can be expressed in bacterial cells such as *E. coli*, insect cells, yeast or mammalian cells (such as Chinese hamster ovary cells (CHO) or COS cells). Other suitable host cells are known to those skilled in the art.

A nucleic acid can be introduced into prokaryotic or eukaryotic cells via conventional transformation or transfection techniques. As used herein, the terms "transformation" and "transfection" refer to a variety of art-recognized techniques for introducing foreign nucleic acids (e.g., DNA) into a host cell, including calcium phosphate or calcium chloride co-precipitation, DEAE-dextran-mediated transfection, lipofection, or electroporation. Suitable methods for transforming or transfecting host cells can be found in Sambrook, et al. (supra), and other laboratory manuals.

For stable transfection of mammalian cells, it is known that, depending upon the expression vector and transfection technique used, only a small fraction of cells may integrate the foreign DNA into their genome. In order to identify and select these integrants, a gene that encodes a selectable marker (e.g., resistance to antibiotics) is generally introduced into the host cells along with the DNA encoding a polypeptide of the invention. Preferred selectable markers include those which confer resistance to drugs, such as G418, hygromycin and methotrexate. A nuclei acid encoding a selectable marker can be introduced into a host cell on the same vector as that encoding a polypeptide of the invention or can be introduced on a separate vector. Stably transfected cells can be identified by drug selection (e.g., cells that have incorporated the selectable marker gene will survive, while the other cells die).

A host cell of the invention, such as a prokaryotic or eukaryotic host cell in culture, can be used to produce (i.e., express) a polypeptide of the invention. Accordingly, the invention provides a method for producing a polypeptide of the invention using the host cells of the invention. In one embodiment, the method comprises culturing the host cell of the invention in a suitable medium such that the polypeptide is produced. In another embodiment, the method further comprises isolating the polypeptide from the medium or the host cell. Methods for cell culture and protein expression and purification can be found, e.g., in Sambrook et al. (supra) and other laboratory manuals.

Compositions

A polypeptide of the invention can be incorporated into pharmaceutical compositions suitable for administration. Such compositions typically comprise the polypeptide and a pharmaceutically acceptable carrier. As used herein, the language "pharmaceutically acceptable carriers" include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, use thereof in the compositions is contemplated. Supplementary active compounds can also be incorporated into the compositions. In addition, the composition may include stabilizing agents such as sodium bicarbonate, BSA, and casein.

A pharmaceutical composition of the invention may be formulated to be compatible with its intended route of administration Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL (BASF; Parsippany, N.J.) or phosphate buffered saline (PBS). In all cases, the composition must be sterile and should be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethelene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the polypeptide in the required amount in an appropriate solvent with one or a combination of ingredients enumerated above, as required, followed by filtered sterilization. Generally, dispersions are prepared by incorporating the polypeptide into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the polypeptide can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring. For administration by inhalation, the compounds are delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compositions can also be prepared in the form of suppositories (e.g., with conventional suppository bases such as cocoa butter and other glycerides) or retention enemas for rectal delivery.

In one embodiment, the polypeptide is prepared with carriers that will protect the polypeptide against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the polypeptide and the particular therapeutic effect to be achieved, and the limitations inherent in the art of compounding such a polypeptide for the treatment of individuals.

A nucleic acid of the invention can be inserted into vectors used as gene therapy vectors. Gene therapy vectors can be delivered to a subject by, for example, intravenous injection, local administration (U.S. Pat. No. 5,328,470) or by stereotactic injection (see, e.g., Chen et al. (1994) Proc. Natl. Acad. Sci. USA 91:3054-3057). The pharmaceutical preparation of the gene therapy vector can include the gene therapy vector in an acceptable diluent, or can comprise a slow release matrix in which the gene delivery vehicle is imbedded. Alternatively, where the complete gene delivery vector can be produced intact from recombinant cells, e.g. retroviral vectors, the pharmaceutical preparation can include one or more cells which produce the gene delivery system.

A pharmaceutical composition of the invention can be included in a container, pack, or dispenser together with instructions for administration.

Uses

G-CSF has been found to be useful in the treatment of conditions where an increase in neutrophils will provide benefits. See, e.g., U.S. Pat. No. 6,790,628. For example, for cancer patients, G-CSF is beneficial as a means of selectively stimulating neutrophil production to compensate for hematopoietic deficits resulting from chemotherapy or radiation therapy. Other indications include treatment of various infectious diseases and related conditions, such as sepsis, which is typically caused by a metabolite of bacteria. G-CSF is also useful alone, or in combination with other compounds, such as other cytokines, for growth or expansion of cells in culture (for example, for bone marrow transplants or ex vivo expansion). G-CSF has been administered to transplant patients as an adjunct to treatment of infection or for treatment of neutropenia (Diflo et al. (1992) Hepatology 16:PA278, Wright et al. (1991) Hepatology 14:PA48, Lachaux et al. (1993) J. Ped. 123:1005-1008, and Colquehoun et al. (1993) Transplantation 56:755-7580).

The invention provides a treatment method involving administering to a subject in need thereof an effective amount of a composition of the invention. A subject to be treated may be identified in the judgment of a subject or a health care professional, and can be subjective (e.g., opinion) or objective (e.g., measurable by a test or diagnostic method). The term "treating" is defined as administration of a substance to a subject with the purpose to cure, alleviate, relieve, remedy, prevent, or ameliorate a disorder, symptoms of the disorder, a disease state secondary to the disorder, or predisposition toward the disorder. An "effective amount" is an amount of the substance that is capable of producing a medically desirable result as delineated herein in a treated subject. The medically desirable result may be objective (i.e., measurable by some test or marker) or subjective (i.e., subject gives an indication of or feels an effect).

The effective amount of a composition of the invention is between 0.001 and 300 mg/kg body weight, 1-4 times every two weeks. The effective amount can be any specific amount within the aforementioned range, wherein the lower boundary is any number of mg/kg body weight between 0.001 and 299, inclusive, and the upper boundary is any number of mg/kg body weight between 0.002 and 300, inclusive. The effective amount is useful in a monotherapy or in combination therapy for the treatment of G-CSF-related disorders. In particular, a dose of 5 µg/kg body weight may be used for human injection and a dose 4 of 50 µg/kg of body weight may be used for oral administration in human. As the skilled artisan will appreciate, lower or higher doses than those recited above may be required. Effective amounts and treatment regimens for any particular subject (e.g., a mammal such as human) will depend upon a variety of factors, including the age, body weight, general health status, sex, diet, time of administration, rate of excretion, drug combination, the severity and course of the disease, condition or symptoms, the subject's disposition to the disease, condition or symptoms, and the judgment of the treating physician or veterinarian.

In particular, the invention provides a method of enhancing transport of G-CSF into or across gastrointestinal (GI) epithelial cells. The method involves contacting GI epithelial cells with a polypeptide of the invention, e.g., through oral administration, such that the polypeptide is transported into or across the cells through the TfR pathway.

The invention also provides a method of enhancing transport of a polypeptide into or across GI epithelial cells in general. The method involves contacting GI epithelial cells with a polypeptide operably linked to a Tf domain. The fusion protein is transported into or across GI cells through the TfR pathway. It is more effective than transport of the polypeptide itself. The molecular weight of the polypeptide is at least 10 kD (i.e., any number equal to or bigger than 10 kD), and the size of the fusion protein is no more than 200 nm (Rejman et al. (2004) Biochem. J. 377:159-169).

The invention also provides another general method of enhancing transport of a polypeptide into or across a GI epithelial cell (e.g., by oral administration). The method involves contacting a GI epithelial cell with a recombinant protein containing a polypeptide operably linked to a Tf domain under conditions that allow transport of the Tf-linked polypeptide into the cell through TfR or transport of the Tf-linked polypeptide across the cell through TfR via transcytosis. The ability of the Tf inked polypeptide to be transported into a cell expressing a Tf gene or the ability of the Tf-linked polypeptide to be transported across a cell expressing a TfR gene via transcytosis is higher than that of the polypeptide; alone. The polypeptide may include, e.g., an insulin domain, growth hormone domain, erythropoietin domain, interferon (e.g., IFN-α) domain, interleukin (e.g., IL-2) domain, and immunoglobulin or its fragment (e.g., Fab and sFv) domain.

TfR-mediated transcytosis in oral delivery of insulin-transferrin (In-Tf) chemical conjugate has been demonstrated in cultured epithelial cells and in animal models (16). Comparing to a small protein such as insulin (~8 kD), it is unexpected that G-CSF (~20 kD), a protein much bigger than insulin, can also be transported into GI cells through TfR-mediated transcytosis. Further unexpected is that G-CSF can be subsequently released into the bloodstream to promote neutrophil proliferation.

G-CSF-Tf conjugates can be prepared by coupling G-CSF with Tf via a chemical linkage. Although they have been shown by the inventors to be bioavailable via oral administration, they are mixtures of heterogeneous protein aggregates and, consequently, impure. They are not suitable for large-scale production, either. In contrast, recombinant G-CSF-Tf protein can be produced in high purity and large quantity. Surprisingly, as shown in Examples 1 and 2 below, recombinant G-CSF-Tf protein exhibited a higher efficacy than the chemical conjugate in BDF1 mice. The half-life of Tf is longer than that of G-CSF. The G-CSF-Tf fusion protein shows a longer half-life than G-CSF alone. Without binding to any theory, a G-CSF-Tf conjugate may dissociate inside a cell or inside the body of a subject. For example, G-SF and Tf linked through a disulfide bond dissociates when the disulfide bond is reduced. A G-CSF-Tf recombinant protein, on the other hand, may remain intact inside a cell or inside the body of a subject. The recombinant protein may have a longer half-life than the conjugate and therefore increased efficacy.

The development of an orally bioavailable G-CSF has the potential to provide great benefit to patients under sustained G-CSF dosing regimes. The following examples are intended to illustrate, but not to limit, the scope of the invention. While such examples are typical of those that might be used, other procedures known to those skilled in the art may alternatively be utilized. Indeed, those of ordinary skill in the art can readily envision and produce further embodiments, based on the teachings herein, without undue experimentation.

EXAMPLES

Example 1

The Transepithelial Transport of a G-CSF-Transferrin Conjugate in Caco-2 Cells and its Myelopoietic Effect in BDF1 Mice Materials and Methods
Caco-2 Cell Culture Caco-2 cells (American Type Culture Collection, Rockville, Md.; passage number 20) were grown on 0.4 μm pore-size polycarbonate Transwell (Costar, Cambridge, Mass.) filters to confluence in Dulbecco's modified eagle media supplemented with 10% FBS, glutamine, non-essential amino acids, penicillin and streptomycin. All cell culture reagents were obtained from Invitrogen/Life Technologies (Carlsbad, Calif.). The monolayers were allowed to differentiate for seven days after reaching confluence. The transepithelial electrical resistance was measured with an epithelial voltammeter (EVOM, World Precision Instruments, West Haven, Conn.). The monolayers typically established maximum resistances of 500 Ωcm$^2$.

Preparation of Tf-G-CSF Conjugate

Human G-CSF was cloned by RT-PCR from human bladder carcinoma cell line 5637 (ATCC), as described by Souza et al. ((1986) (17) and subsequently sub-cloned into the pGEX-4T-1 expression vector (Amersham Pharmacia) as a GST fusion protein in BL21 E. coli. The expression of the fusion protein was accomplished by growing the transformed BL21 bacteria in LB broth at 37° C. until A600 nm=0.5 followed by induction of GST-G-CSF synthesis with 0.1 mM isopropyl β-D-thiogalactoside (IPTG) for four hours. The bacteria was then harvested, resuspended in PBS, and lysed via sonication. Triton X-100 was added to the sonicate for a final concentration of 1% and gently mixed on ice for 30 min. GST-G-CSF fusion protein was purified from the crude sonicate with Glutathione-Sepharose 4B, washed extensively with PBS, and incubated overnight with 5 U/mg of thrombin (Amersham) to liberate G-CSF from the matrix. The minute amount of thrombin, was removed from the eluent via. Benzamidine Sepharose 6B (Amersham) treatment. The purity of G-CSF was verified via SDS-PAGE and the yield was estimated by measuring the absorbance at 280 nm, with an extinction coefficient of 15820 M$^{-1}$. The yield of G-CSF from this procedure was typically 0.5 mg/L.

G-CSF was covalently linked to iron-loaded human Tf through disulfide linker chemistry as previously described (18). Briefly, a 20 mg/mL solution of iron-loaded Tf in PBS (pH 7.4) was mixed with a ten-fold molar excess of the hetero-bifunctional cross-linking agent N-succinimidyl 3-(2-pyridyldithio)propionate (SPDP) (Pierce, Rockford, Ill.) at 4° C. for 30 min. The final ratio of SPDP to Tf was determined to be 1:1. G-CSF was next modified with the homo-bifunctional linker agent 1,4-Di-[3'-(2'-pyridyldithio)propionamido]butane (DPDPB). The ratio of DPDPB to G-CSF was determined to be 1:1. SPDP-Tf was reduced with 25 mM dithiothreitol (Sigma) reacted with 10-fold molar excess DPDPB-G-CSF to form the G-CSF-Tf conjugate. The reaction was quenched by addition of 1 mg/mL of N-ethylmaleimide, followed by overnight dialysis against PBS (pH 8.0, 4° C.). The Tf-G-CSF conjugate was purified by gel filtration on a Sephacryl S-200 column.

Assessment of Apical-to-Basolateral Transcytosis of $^{125}$I-Tf, $^{125}$I-G-CSF and $^{125}$I-G-CSF-Tf Across Caco-2 Cell Monolayers Iodinated G-CSF was obtained for the in vitro transport studies by purifying r-metHu-G-CSF from commercial filgrastim preparations (Amgen). Specifically, filgrastim solution was dialyzed against 10 mM acetate buffer to remove excipients. Following this, the recovered solution was concentrated in Amicon 3,000 MWCO concentrators, and the G-CSF was iodinated by the chloramine-T catalyzed method. G-CSF and Tf-G-CSF were iodinated using the chloramine-T method as described above for the preparation of $^{125}$I-Tf. Transport studies were conducted on two week-old Caco-2 monolayers, 6 or 7 days after they had exhibited signs of tight junction development. Monolayers were washed once with DMEM and incubated at 37° C. for 45 min to deplete endogenous Tf. Media were subsequently replaced and the monolayers were treated with $^{125}$I-Tf, $^{125}$I-G-CSF or $^{125}$I-Tf-G-CSF in the apical compartment (1.5 μg/mL). Non-specific transport was measured in parallel by the inclusion of 100-fold molar excess of unlabeled Tf. At 2, 4, and 6 h post-dosing, 500 μL samples were collected from the basolateral compartment and replenished with an equal volume of fresh DMEM. Samples were subjected to 15% trichloroacetic acid (TCA) precipitation and radioactivity of the pellet was measured with a Packard gamma counter. The extent of TfR-mediated transcytosis was determined by subtracting non-specific transport (inclusive of excess unlabeled Tf) from total transport.

Analysis of Transcytosed Proteins

Transcytosed proteins were analyzed in separate transport studies via size exclusion chromatography and G-CSF-dependent cell proliferation assays. Basolateral fluids were collected after a six-hour transport study as described above and subjected to Sephacryl S-200 column chromatographic analysis, where stock $^{125}$I-labeled proteins (i.e., $^{125}$I-Tf, $^{125}$I-G-CSF and $^{125}$I-G-CSF-Tf) were used for determination of appropriate elution volumes. Biological activity assays were conducted for transcytosed $^{125}$I-G-CSF and $^{125}$I-G-CSF-Tf by measuring proliferation of the murine myeloblastic cell line NFS-60 (19). NFS-60 cells that had been cultured in RPMI-1640 medium, supplemented with both 10% FBS and 10% WEHI-3 (ATCC) conditioned medium (CM), were washed three times with serum- and WEHI-3 CM-free RPMI-1640 and aliquoted to 96 well microtiter plates at a density of $1\times10^5$ cells/mL. These cells were spiked with 20 μL of medium that had been previously recovered from the basolateral compartments in the conjugate transport studies and concentrated 10-fold with a Centricon centrifugal concentrator apparatus (Amicon, Bedford, Mass.). The samples were incubated at 37° C. in a 5% $CO_2$ incubator for 48 h. A MTT (3-(4,5-dimethylthiazol-2-yl)-2,5-diphenyl tetrazolium bromide) assay was subsequently performed essentially as previously described by Mosmann ((1983)(20). Briefly, cells were incubated with phenol-red free RPMI media (Invitrogen, Carlsbad, Calif.) containing 1 mg/mL MTT for 2 h. The formazan crystals that formed were then dissolved in isopropanol (Sigma) and absorbance was measured at 570 nm on a Dynatech M70 microplate reader.

In Vivo Studies

Specific pathogen-free BDF1 male mice (Charles River Laboratories, Wilmington, Mass.) were used at 6-8 weeks of age. BDF1 mice were chosen due to their relatively robust stimulatory response to human G-CSF. The mice were allowed to acclimate for several days prior to beginning experiments. Animal experiments were compliant with the 'Principles of Laboratory Animal Care' (NIH Publication #85-23) and approved by the IACUC at USC. The mice were fasted for 12 h prior to dosing. The mice were individually weighed and the dosages were adjusted accordingly. The mice weight was typically between 18-20 g. The treatment groups (n=5) received a single subcutaneous (SC) injection or oral administration (via gavage needle) on day 0 with G-CSF-Tf, filgrastim, or vehicle control (PBS). Since the molecular weight of G-CSF-Tf is about 5-fold higher than filgrastim, G-CSF-Tf was administered at 5 mg/kg SC and filgrastim was given at 1 mg/kg SC. Similarly, G-SCF-Tf was given at a rate of 50 mg/kg orally and filgrastim was given at 5 mg/kg orally. The concentrations of the dosing solutions were adjusted so that the dosage volume in all cases was 100 μL. G-CSF-Tf and filgrastim were formulated with sodium bicarbonate (30 mg/mL) in PBS prior to oral administration. Sodium bicarbonate was included to neutralize stomach acid in order to prevent hydrolysis of the protein-drug.

Blood samples were collected daily from the tails of the mice into micro-tubes that had been pretreated with heparin. Total white blood cell counts (WBC) were performed manually with a hemacytometer. The samples were diluted 20-fold and lysed in an acidic crystal-violet solution (0.1% crystal violet, 1% acetic acid, in water) prior to being loading in the hemacytometer. The percentage of poly-morphonuclear neutrophils (PMN) amongst the leucocytes was determined manually with Wright-stained blood-smear glass slides that were examined with a 100× oil immersion lens on an Olympus BH-2 microscope. The absolute number of neutrophils was determined by applying the observed PMN percentage against the total WBC count for each sample (21).

Statistical Analyses

Data are presented as mean (±SEM). One-way analysis of variance (ANOVA) was used to determine statistical significance among group (n≧3) means using Tukey's post-hoc tests. $p<0.05$ was considered significant.

Results

Apical-to-Basolateral Transcytosis of G-CSF-Tf and Tf Across Caco-2 Monolayers

Two-week old Caco-2 monolayers; exhibiting TEER levels of approximately 500 $\Omega cm^2$, were dosed with 1.5 μg/mL of $^{125}$I-G-CSF-Tf or $^{125}$I-G-CSF in the apical compartments of 6-well Transwells. As shown in FIG. 1, monolayers that received G-CSF-Tf exhibited significantly higher TfR-mediated transcytosis compared to the monolayers that received $^{125}$I-G-CSF. For example, after six hours, the amount of transported $^{125}$I-G-CSF-Tf was 7.8-fold higher than $^{125}$I-G-CSF (9.3±0.8 fmol/well $^{125}$I-G-CSF-Tf, 1.2±0.7 fmol/well $^{125}$I-G-CSF) (FIG. 1). In addition, the transport rate was also significantly higher, with $^{125}$I-G-CSF-Tf transported at 1.7 fmol/well·$hr^{-1}$ and $^{125}$I-G-CSF transported at 0.3 fmol/well·$hr^{-1}$. Non-specific $^{125}$I-G-CSF-Tf and $^{125}$I-G-CSF transport was significantly lower than TfR-mediated transcytosis, with nonspecific transport composing 25% and 27% of the total transport for $^{125}$I-G-CSF-Tf and $^{125}$I-G-CSF, respectively.

Chromatographic Analysis of Transcytosed G-CSF-Tf

Figure 2:
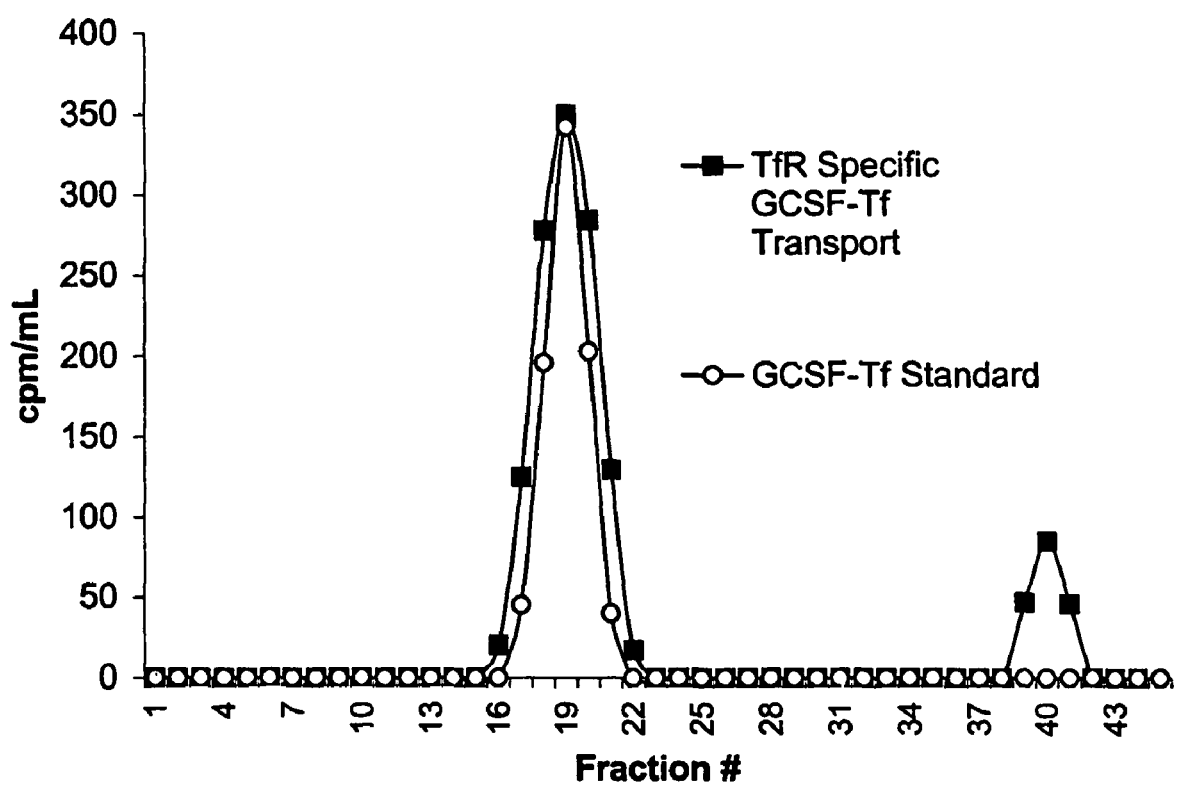
FIG. 2 is a gel filtration chromatogram of TfR-mediated transcytosed $^{125}$I-G-CSF-Tf. Apical compartments of Caco-2 monolayers were dosed with 1.5 μg/mL $^{125}$I-G-CSF-Tf and the basolateral media collected after six-hour incubation at 37° C. The basolateral samples were applied to a 40 mL Sephacryl 200 column, eluted with PBS (pH-7.4), and compared to the standard $^{125}$I-G-CSF-Tf solution. The fractions (1 mL) were subsequently counted on a Packard gamma counter.

Apical compartments of Caco-2 monolayers were dosed with 1.5 μg/mL $^{125}$I-G-CSF-Tf and the basolateral media collected after six-hour incubation at 37° C. Samples were subjected to size exclusion chromatography analysis. When samples recovered from the basolateral compartments were applied to a 40 ml Sephacryl-200 column, the major recorded peak coincided with the $^{125}$I-G-CSF-Tf column standard at fraction 19, indicating that the molecular weight of the $^{125}$I-G-CSF-Tf (recovered post-TfR-mediated transcytosis) was identical to the molecular weight of the $^{125}$I-G-CSF-Tf standard (FIG. 2). The extent of degradation appeared to be minor, with relatively little small-molecule products appearing around fraction 40, accounting for 13% of total radioactivity.

Figure 3:
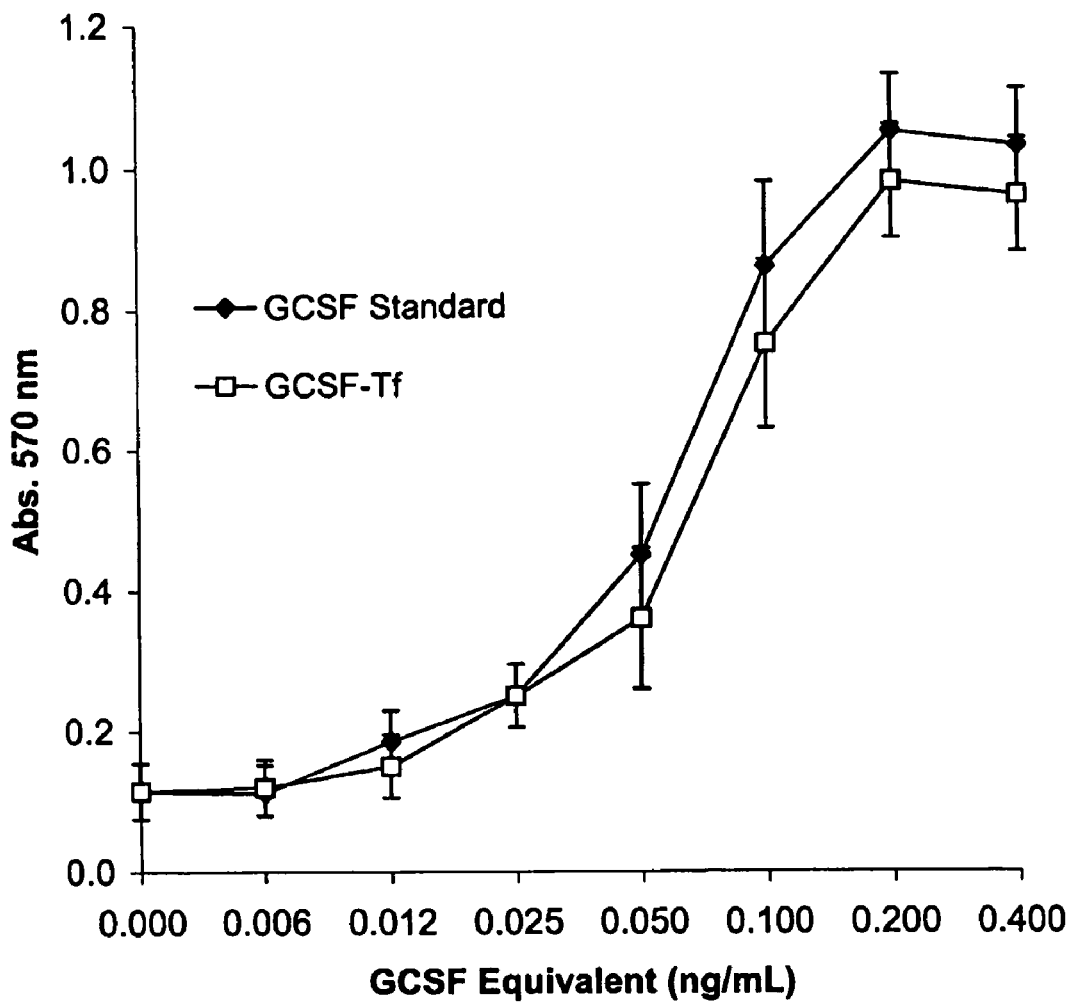
FIG. 3 shows evaluation of biological activity of transcytosed G-CSF-Tf. Apical compartments of Caco-2 monolayers were dosed with 1.5 μg/mL $^{125}$I-G-CSF or $^{125}$I-G-CSF-Tf and the basolateral media collected after six-hour incubation at 37° C. Biological activity assays were conducted for transcytosed $^{125}$I-GSCF-Tf after reduction of the disulfide linkage (25 mM DTT treatment for 15 min) by measuring proliferation of the murine myeloblastic cell line NFS-60 via. MTT assay. Results are also shown for G-CSF control (Neupogen).

Analysis of Biological Activity of Transcytosed $^{125}$I-G-CSF-Tf in Caco-2 Monolayers The biological activity of transcytosed conjugate was next determined through a NFS-60 MTT proliferation assay. Basolateral media was collected as described above after a six-hour transport experiment across Caco-2 monolayers. The samples were then sterile filtered, normalized for G-CSF content, and used as assay substrate. The sample was subjected to reducing conditions prior to the assay (25 mM DTT, 15 min) in order to mimic reducing conditions that would encountered by the conjugate in vivo. The biological activity of the recovered $^{125}$I-G-CSF-Tf conjugate closely matches the activity of the G-CSF standard, with 0.1 ng/mL G-CSF equivalents displaying an absorbance (570 nm) of 0.87±0.08 and 0.78±0.06 for the G-CSF standard and the reduced $^{125}$I-G-CSF-Tf conjugate, respectively (FIG. 3).

Neutrophil Proliferation in BDF1 Mice Dosed with Subcutaneous and Oral G-CSF-Tf

Figure 4:
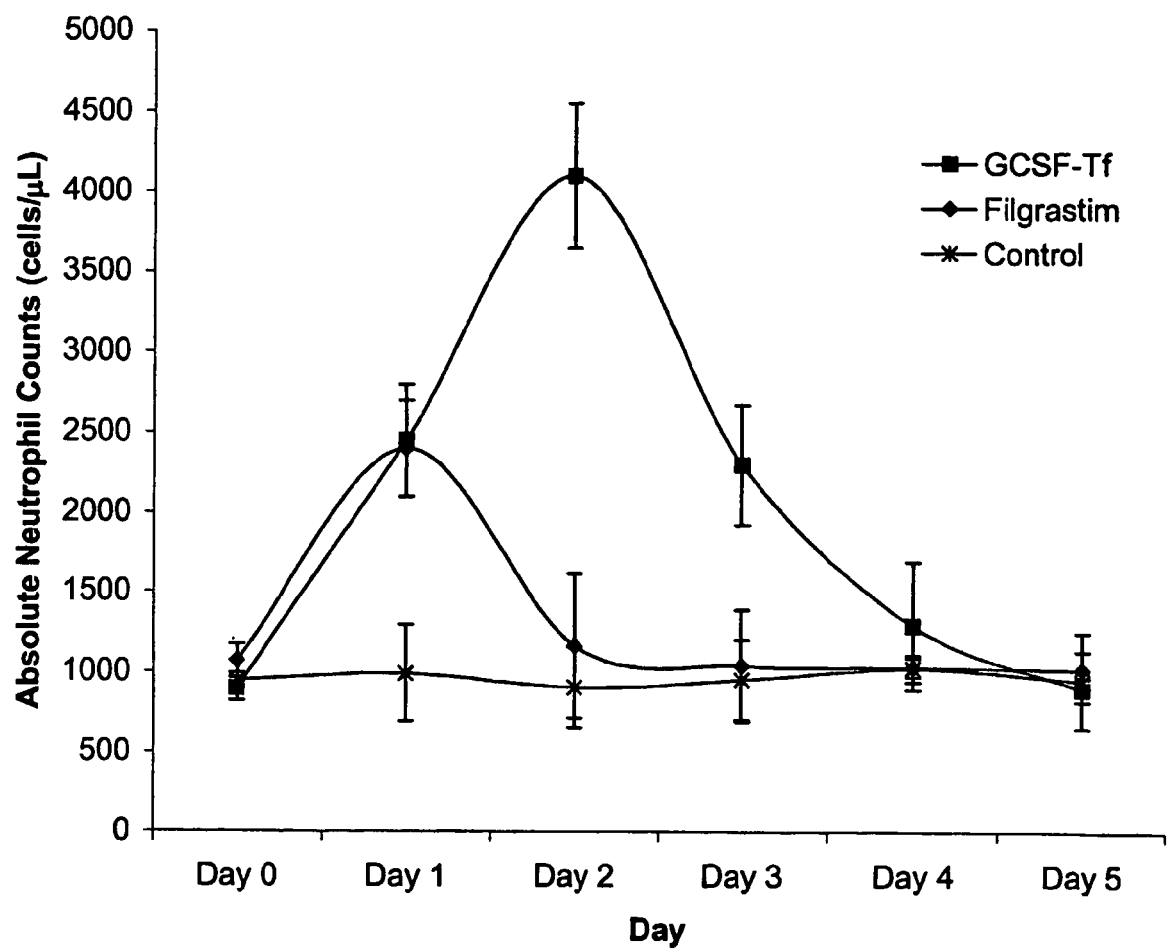
FIG. 4 demonstrates myelopoietic effect of subcutaneously administered G-CSF-Tf. G-CSF-Tf (5 mg/kg), filgrastim (1 mg/mL), or control vehicle was administered subcutaneously to 8-week old male BDF1 mice. Absolute neutrophil counts were determined daily.

BDF1 mice were given 1 mg/kg filgrastim, 5 mg/kg G-CSF-Tf, or control vehicle subcutaneously. The day of dosage administration was denoted as day 0. By day 1, both the G-CSF-Tf and filgrastim treatment groups exhibited an increase in absolute neutrophil counts (2420±450 cells/μL for the G-CSF-Tf treatment group and 2375±400 cell/μL for the filgrastim treatment group) (FIG. 4). However, by day 3 there was a marked significant difference between the two treatment groups, with 4100±510 cells/μL for the G-CSF-Tf treatment group and 1200±385 cells/mL for the filgrastim treatment groups. The neutrophil levels remained elevated for the G-CSF-Tf treatment group, relative to control and filgrastim groups, until day 3 and then returned to normal levels by day 4.

Figure 5:
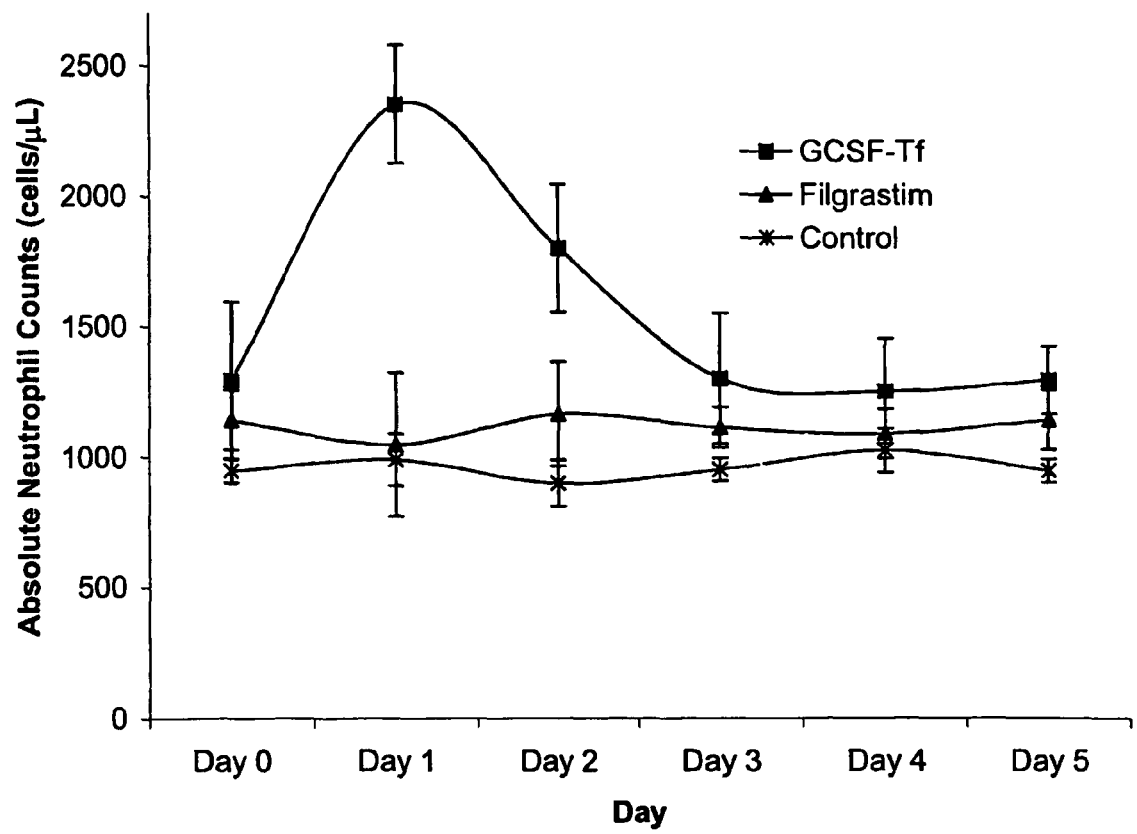
FIG. 5 depicts myelopoietic effect of orally administered G-CSF-Tf. G-CSF-Tf (50 mg/kg), filgrastim (10 mg/kg), or control vehicle was administered orally by gavage needle to 8-week old male BDF1 mice. Absolute neutrophil counts were determined daily.

For the oral dosing experiments, BDF1 mice were given 10 mg/kg filgrastim, 50 mg/kg G-CSF-Tf, or control vehicle by gavage needle. The mice that received G-CSF-Tf demonstrated a statistically significant elevation in absolute neutrophil counts by day 1 with 2350±225 cells/μL (FIG. 5). In contrast, oral administration of filgrastim did not result in a statistically significant change in neutrophil levels compared to control (1080±0.280 cells/μL and 990±95 cells/μL for filgrastim and control groups on day 1, respectively). Absolute neutrophil counts continued to be significantly elevated for the G-CSF-Tf treatment compared to control until day 3, when they returned to normal levels.

A dose response experiment was next performed on orally administered G-CSF-Tf. BDF1 mice were given 50 mg/kg, 25 mg/kg, or 12.5 mg/kg G-CSF-Tf orally by gavage needle. The group that received 50 mg/kg demonstrated a similar response as seen in the previous experiment, with 2300±295 cells/μL recorded for absolute neutrophil counts on day 1 (FIG. 6), which was significantly different from the other two treatment groups. There was an indication that the neutrophil counts were elevated for the 25 mg/kg group compared to the 12.5 mg/kg group on day 1 (1400±200 cells/μL and 1030±168 cells/μL for 25 mg/kg and 12.5 mg/kg groups, respectively, $p \leq 0.10$).

DISCUSSION

Caco-2 cell culture model has come to serve as a leading qualitative indicator in screening GI permeability and absorption of therapeutic agents (22-25). In this study, the amount of $^{125}$I-G-CSF-Tf transported in the apical-to-basolateral direction, relative to $^{125}$I-G-CSF, in two-week old Caco-2 monolayers (FIG. 1) was investigated. The data demonstrate that the rate of apical-to-basolateral $^{125}$I-G-CSF-Tf transport is significantly higher than that of $^{125}$I-G-CSF (1.70 fmol/well/hr and 0.25 fmol/well/hr for $^{125}$I-G-CSF-Tf and $^{125}$I-G-CSF, respectively). The enhanced transport of the G-CSF-Tf conjugate, compared to G-CSF, was presumed to be as a result of TfR-mediated transcytosis processes. This was suggested by competitive inhibition studies that demonstrated 80% reduction in $^{125}$I-G-CSF-Tf apical-to-basolateral transport in the presence of 100-fold molar excess unlabeled Tf. Previously, it was demonstrated that an insulin-Tf conjugate is able to be transcytosed across Caco-2 monolayers by TfR-specific processes, while the unconjugated insulin was unable to be transported across Caco-2 monolayers (26). The fact that G-CSF, a much larger protein-drug than insulin, is also able to be transported across Caco-2 monolayers as a Tf-conjugate suggests that TfR-mediated transcytosis may serve as a multi-platform vehicle to deliver proteins of varying sizes.

Efforts were next undertaken to examine the protein-drug downstream after the transcytosis process. The results indicate that G-CSF only suffered from a minor degree of degradation as a result of the TfR-mediated transcytosis process. For example, as shown in FIG. 2, when G-CSF-Tf is recovered from the basolateral compartment, post-TfR-mediated transport, and applied to a 40 mL S-200 column, the major recorded peak coincides with the peak for the G-CSF-Tf standard at fraction number 19. A low level of small molecular weight degradation products can also be seen at fraction number 40, accounting for only 13% of the total applied radioactivity. One can infer from this data that the molecular weight of the G-CSF-Tf conjugate is not altered by the transcytosis process in Caco-2 monolayers and relatively little conjugate is degraded. This result is supported by previous studies that have shown similar results in monolayers of various cell types and for different cargo-proteins (18; 26; 27).

In addition to determination of molecular weight, the biological activity of the transcytosed conjugate was also determined. The conjugate was recovered after a transcytosis experiment from the receiver compartment of Caco-2 monolayers, concentrated ten-fold, and then subjected to a brief mild DTT reduction (25 mM DTT, 15 min) in order to liberate free G-CSF from the conjugate. The DTT reduction also serves to mimic the natural reduction of di-sulfide linked Tf protein-drug conjugates that one would observe in vivo (16). As shown in FIG. 3, the G-CSF that has undergone TfR-mediated transcytosis across Caco-2 monolayers retains almost all of its biological activity relative to control, as measured by the ability to stimulate the proliferation of NFS-60 cells (19) ($ED_{50}$ values of 0.06 ng/mL and 0.07 ng/mL for the G-CSF standard and the transcytosed-G-CSF, respectively). Taken together, these experiments suggest that TfR-mediated transport might be able to deliver protein-based therapeutics that are much larger than insulin (28), across GI epithelial barriers while retaining biological function of the cargo protein.

The in vivo efficacy of G-CSF-Tf was investigated next. Acute doses of G-CSF-Tf, filgrastim, or control vehicle were administered subcutaneously to 6-8 week old BDF1 mice (n=5). Absolute neutrophil counts were performed daily. As can be seen in FIG. 4, the G-CSF-Tf treatment group demonstrated an increased duration of action and significantly higher neutrophil counts (for days 2 and 3) relative to the group receiving filgrastim. G-CSF is known to follow a non-linear pharmacokinetic clearance profile, which is most likely due in major part to receptor-mediated endocytosis (1). The clearance rate of G-CSF, when covalently conjugated to Tf, may be significantly reduced relative to filgrastim. This phenomenon could arise due to several factors. The first is that the conjugation of G-CSF to Tf may reduce or eliminate a predominant means of G-CSF clearance, which is dependent upon the amount of circulating neutrophils (1). In addition, the large molecular weight of the conjugate, relative to G-CSF, should result in reduced renal clearance, which is the other major route of G-CSF elimination. This hypothesis is supported by previous studies that have demonstrated a large decrease in clearance rate when G-CSF has been genetically fused to albumin (3) or when G-CSF has been modified by pegylation (2). In addition, the serum half-life of Tf in mice (40 h) (29) is much longer than the terminal half-life of G-CSF (~2.5 h) (30). It is possible that the G-CSF-Tf conjugate may have a clearance rate that is more similar to Tf than G-CSF, as Tf is predominantly recycled after binding to its receptor. G-CSF may also be slowly released from the conjugate as the disulfide linkage is reduced, as has been seen for other disulfide linked protein-drug conjugates (16; 31), enabling sustained neutrophilic leukocytosis relative to filgrastim. Another possibility is that subcutaneous administration of G-CSF-Tf may result in the binding of the conjugate to TfR in the interstitial tissues, creating a depot effect. G-CSF would also be slowly released from the site of administration in this situation, resulting in a sustained therapeutic effect.

Figure 6:
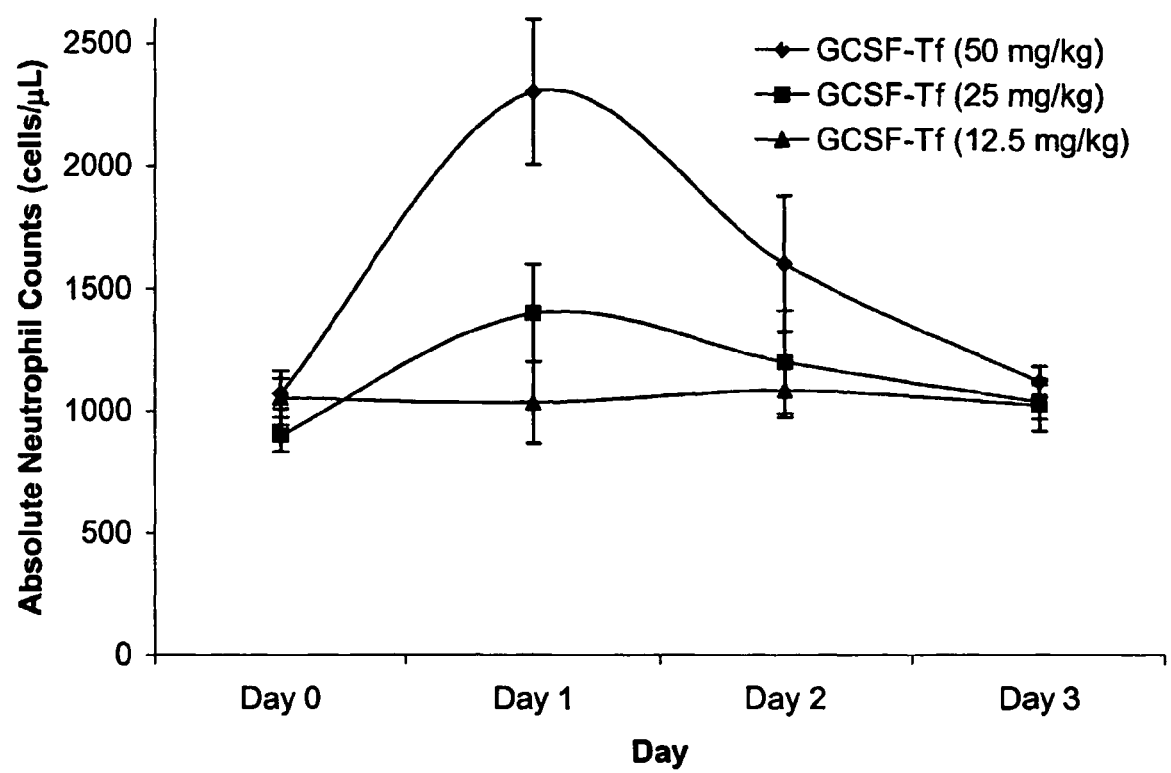
FIG. 6 shows dose response effect of orally administered G-CSF-Tf G-CSF-Tf was given orally to 8-week old BDF1 mice by gavage needle at concentrations of 50 mg/kg, 25 mg/kg, and 12.5 mg/kg. Myelopoietic effect was determined by daily absolute neutrophil counts.

In light of our findings that G-CSF-Tf can be actively transported across Caco-2 monolayers (FIGS. 1-3), the feasibility of using Q-CSF-Tf in an oral route of administration was investigated. BDF1 mice (6-8 week old) were given G-CSF-Tf (50 mg/kg) or filgrastim (10 mg/kg) by gavage needle. Absolute neutrophil counts were performed as in the subcutaneous administration studies. Oral G-CSF-Tf was able to elicit a significant increase in neutrophil counts (for days 1 and 2) while filgrastim had no effect when administered orally (FIG. 5). In addition, G-CSF-Tf appears to have a dose-specific response when administered orally, providing evidence that G-CSF-Tf has a true pharmacological effect (FIG. 6). Since G-CSF will only have a myelopoietic effect if it is absorbed into the bloodstream, this data suggests that G-CSF-Tf has a statistically significant oral bioavailability. In addition, when comparing the area under the curve of subcutaneously and orally administered G-CSF-Tf (FIGS. 4 and 5), the oral bioequivalence of G-CSF-Tf is about 4%. TfR is known to be highly expressed in the small intestine and Tf is absorbed by the GI epithelium as a part of normal physiological processes (15; 32) and Ron and Enn (2000) Blood 96:4020-4027). G-CSF-Tf may be taken up by similar processes. In addition, this result is supported by the previous report that an orally administered insulin-Tf conjugate is able to elicit a hypoglycemic effect in diabetic rats while free insulin had no effect (16). G-CSF-Tf may therefore be able to be orally absorbed by TfR-specific transcellular transport processes.

In conclusion, the creation a G-CSF-Tf conjugate that is, transported across Caco-2 monolayers by TfR-mediated transcytosis at a rate that is several-fold higher than non-specific apical-to-basolateral G-CSF flux is described. G-CSF-Tf is also recovered from the receiver compartment of Caco-2 monolayers with the molecular weight intact and retains full biological function. The conjugate also exhibits a prolonged myelopoietic effect in mice compared to filgrastim. This result was observed in both subcutaneous and oral administration. The mechanism whereby G-CSF-Tf exhibits a prolonged therapeutic effect as well as the in vivo kinetics of G-CSF release from the conjugate remain to be determined, however previous studies have indicated that conjugation to the relatively large molecular weight Tf may reduce clearance rate of G-CSF. In addition to the improved pharmacokinetic characteristics of G-CSF-Tf, the development of an orally bioavailable G-CSF has the potential to provide great benefit for patients that are indicated for a chronic G-CSF dosing regime.

Example 2

Recombinant G-CSF-Transferrin Fusion Proteins

Materials and Methods
Construction of G-CSF-Tf Plasmid

Human G-CSF cDNA with secretion signal was cloned by RT-PCR from human bladder carcinoma 5637 (ATCC). Human transferrin cDNA was subcloned from the plasmid TFR27A (ATCC). Expression plasmid containing both transferrin and G-CSF sequences in a single reading frame was constructed using the mammalian expression vector pcDNA3.0. A dipeptide linker, Leu-Glu, was introduced between the two proteins as a short connection. The sequence was confirmed by DNA sequencing.
Engineer and Isolate Recombinant G-CSF-Tf Fusion Construct For the production of fusion protein, HEK293 was seeded in 6-wells plates using MEM medium supplemented with 10% FBS. After reaching 85-90% confluence, the cell monolayers were transiently transfected by the LipofectAMINE™ mediated method as described by the vendor (Invitrogen). After 4 to 6 hours incubation, the transfection medium in each well was changed to CD293 chemical defined protein free media. The transfected cells were cultured in protein free medium for 5 days before the conditioned medium was collected. G-CSF-Tf fusion protein was isolated by precipitation in 50% saturation of ammonium sulfate. The stably transfected clones were selected in MEM medium with 400 mg/ml G418.

Western Blotting Analysis

Samples were separated in 8% SDS-PAGE. The proteins were transferred to a cellulose nitrate membrane (Millipore). Goat antibodies against human serum transferrin (1:10,000) and human G-CSF (1:1,000) were used as primary antibodies respectively. Horseradish peroxidase-conjugated anti-goat immunoglobulin antibody (1:10,000) was used as secondary antibody, and peroxidase activity was detected by enhanced chemiluminescence (ECL, Amersham).

In vitro Assay of G-CSF Activity

The G-CSF activity of the fusion protein was measured by NFS-60 proliferation assay (Shirafuji et al. (1989) Exp. Hematol. 17:116-119). NFS-60 cells were washed three times with RPMI-1640/10% FBS and aliquots of cell suspension were added to 96-well microtiter plates at a density of $1 \times 10^5$ cells/ml. Subsequently, 10 μl of 10 fold serial dilutions of the filgrastim and fusion protein was added to each well. The plates were incubated at 37° C. in a 5% $CO_2$ incubator for 48 hours and MTT (3-(4,5-dimethylthiazol-2-yl)-2,5-diphenyl tetrazolium bromide) assay was subsequently performed to measure the proliferation of NFS-60 cells as described by Mosmann. (Mosmann (1983) J. Immunological Methods 65:55-63).

Transferrin Receptor Binding Assay on Caco-2 Monolayer

Purified G-CSF-Tf fusion protein was radiolabeled with $^{125}I$ (ICN, Irvine, Calif.) using chloramines-T catalyzed iodination (Hunter et al. (1962) Nature 194:495-496). Confluent Caco-2 monolayers in 12-well cluster plates were washed with ice cold PBS for three times, then incubated in serum-free culture media (DMEM) supplemented with 0.1% BSA at 37° C. for 30 min to remove the endogenous transferrin. The mixture of 3 μg/ml labeled fusion protein with 3-, 10-, and 30-fold excess of unlabeled transferrin in DMEM with 0.1% BSA were added to different wells. After 30 min of incubation at 4° C., the medium was removed, and the cell monolayers were washed thrice with ice cold PBS. Subsequently, each cell monolayer was dissolved in 1 ml of 1 M NaOH, and the cell lysate from each well was counted by using a gamma counter.

In Vivo Myelopoietic Effect of G-CSF-Tf Fusion Protein in Male BDF1 Mice Via Subcutaneous or Oral Delivery Route Male BDF1 mice (Charles River Laboratories, Wilmington, Mass.), 6-8 weeks of age, were used throughout. Animal experiments were compliant with the 'Principles of Laboratory Animal Care' (NIH Publication #85-23). The mice were allowed to acclimate for several days prior to starting of the experiment. Before dosing, the mice were fasted for 12 hours. For subcutaneous (SC) group, fusion protein (5 mg/ml), filgrastim (1 mg/ml) were injected subcutaneously on day 0. For the oral administration group, fusion protein (50 mg/kg), filgrastim (10 mg/kg) were given via a gavage needle on day 0. Similar molar amount of filgratim and G-CSF-Tf fusion protein was given. (filgratim is 18.8 kDa, while fusion protein is about 100 kD).

Blood samples were collected daily from the tail vein and diluted 20-fold and lysed in an acidic crystal-violet solution (0.1% crystal violet, 1% acetic acid, in water). The total number of white blood cells was counted manually in the hemacytometer. The percentage of neutrophils (PMN) amongst the leucocytes was determined manually by Wright-stained blood smear glass slides under an Olympus BH-2 microscope. The absolute neutrophil count (ANC) was determined by multiplying the total WBC count by the PMN percentage.

Results

Expression, Purification and Biochemical Characterization of the Fusion Protein

Figure 7:
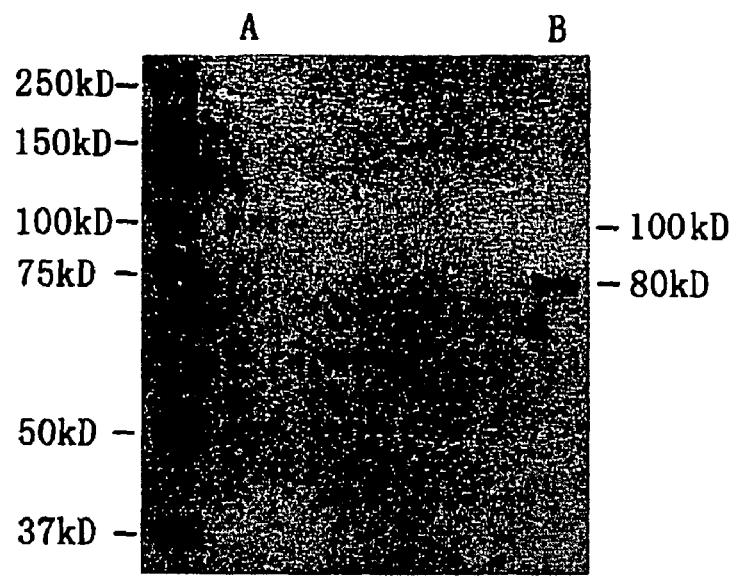
FIG. 7 shows SDS-PAGE of purified recombinant fusion protein. Lane A: fusion protein; lane B: transferrin.

After five days in CD293 medium, the conditioned medium from transfected HEK293 cell cultures was collected. The fusion protein was analysis by using SDS-PAGE (FIG. 7). After ammonium sulfate precipitation procedure, only one major band, with a molecular weight of approximately 100 kD, was detected with Coomassie blue stain. This observation agrees with the expected molecular weight of the fusion, protein. (Transferrin is about 80 kD, and G-CSF is about 19.6 kD. The fusion protein should be 99.6 kD.)

From the conditioned medium of the stable transfected HEK293 cells, an additional protein band between 50 kD and 75 kD, was detected. This protein was also found in the CD293 condition medium of untransfected HEK293 cells. Therefore, this protein most likely is an endogenous secreted protein of HEK293 cells.

Figure 8:
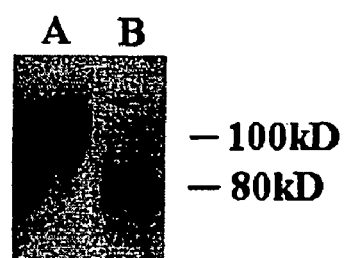
FIG. 8a shows that the recombinant fusion protein is recognized by anti-Tf antibodies. Western-blot using anti-Tf antibody. Lane A: fusion protein; lane B: transferrin.
FIG. 8b shows that the recombinant fusion protein is recognized by anti-G-CSF antibodies. Western-blot using anti-G-CSF antibody. Lane A: fusion protein; lane B: G-CSF control.
Figure 8:
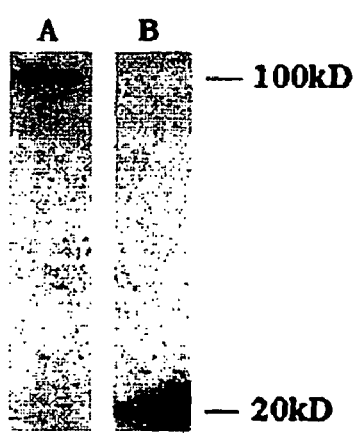

The composition of the secreted fusion protein was confirmed by using both anti-transferrin and anti-G-CSF antibodies in Western-blot analysis (FIG. 8). FIG. 8 (a) shows that the fusion protein (Lane A) was recognized by anti-transferrin antibody. FIG. 2 (b) shows the fusion protein (lane A) was recognized by anti-human G-CSF monoclonal antibody also.

G-CSF and Transferrin Activity of the Fusion Protein In Vitro

Figure 9:
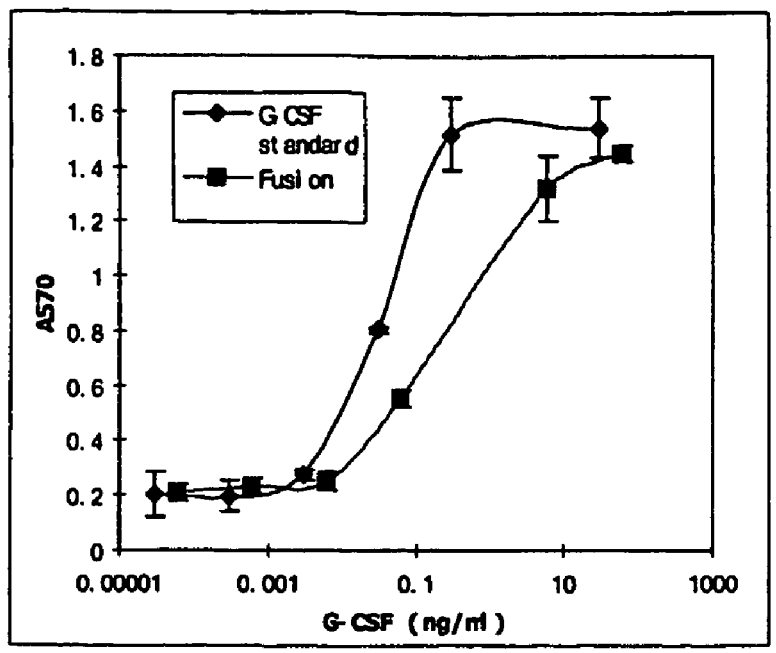
FIG. 9 shows in vitro evaluation of G-CSF activity of purified G-CSF-Tf recombinant fusion protein. The proliferation of the murine myeloblastic cell line NFS-60 was measured via MTT assay. The concentration of the fusion protein was expressed as the G-CSF equivalence. Error bars represent standard deviation.

After ammonium sulfate precipitation purification, the fusion protein was assayed for G-CSF activity by determining its ability to stimulate NFS-60 cell proliferation (FIG. 9). The fusion protein was sterilized by filtration, normalized for G-CSF equivalency, and added to NFS-60 cell culture medium. The biological activity of the fusion protein was approximately one tenth of the commercial G-CSF. The EC50 of filgrastim control is about 0.1 ng/ml, while the EC50 of the fusion protein is about 1 ng/ml (G-CSF equivalent).

Figure 10:
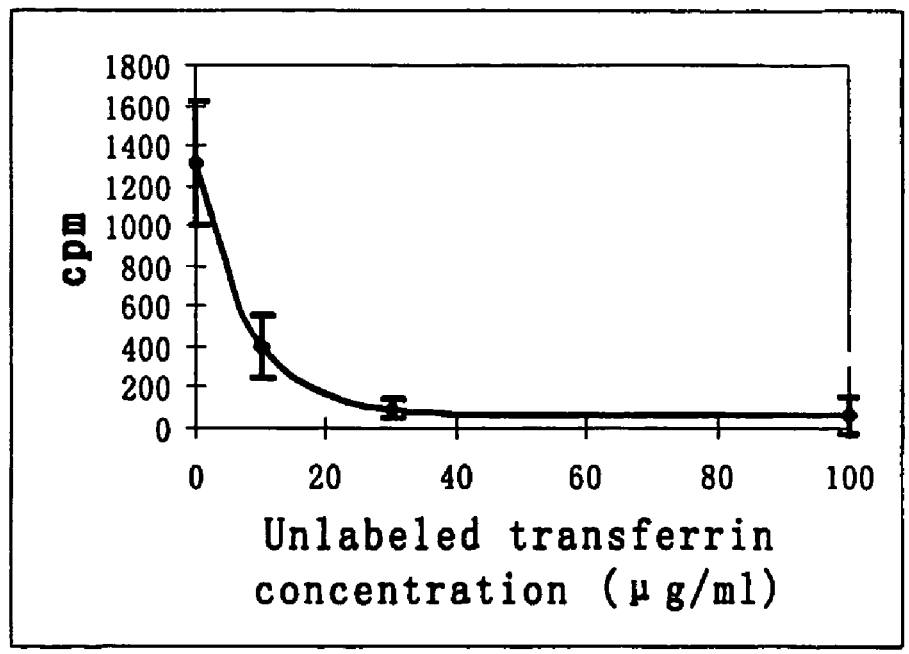
FIG. 10 shows in vitro evaluation of Tf activity of purified G-CSF-Tf recombinant fusion protein. $^{125}$I labeled fusion protein (3 μg/ml in serum-free medium with 1 mg/ml BSA) was added to Caco-2 monolayer. Different concentrations of unlabeled transferrin were added to compete for transferrin receptors. Specific binding was shown. Error bar represents SEM (n=3).

The transferrin receptor binding ability of the G-CSF-Tf fusion protein was determined by surface binding study (FIG. 10). It showed that the binding of $^{125}$I-labeled fusion protein could be blocked by unlabeled transferrin. This result indicates that the G-CSF-Tf fusion protein still possesses the binding capacity to the transferrin receptor.

Figure 11:
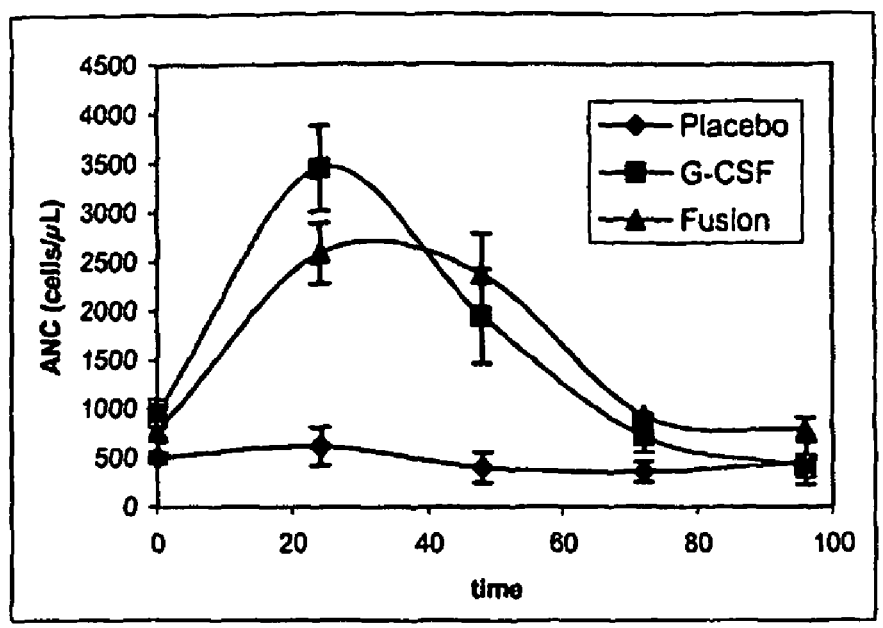
FIG. 11 shows myelopoietic effect of subcutaneously administered recombinant fusion protein, G-CSF, or control. G-CSF-Tf fusion protein or G-CSF was administered to BDF1 mice by subcutaneous injection at a dose of 5 or 1 mg/kg, respectively. Error bar represents SEM (n=3 for control and G-CSF, n=4 for fusion protein).

Effect of Subcutaneously and Orally Administered G-CSF-Tf Fusion Protein on Neutrophil Proliferation in BDF1 Mice BDF1 mice were given 1 mg/kg filgrastim, 5 mg/kg G-CSF-Tf fusion protein, or PBS control subcutaneously. The day of the protein administration was denoted as day 0. As shown in FIG. 11, the fusion protein has a similar therapeutic effect as filgrastim. And the time-effective curves of the fusion protein and filgrastim have similar shape. Both of them reached the maximum effect at 24 hours post administration.

Figure 12:
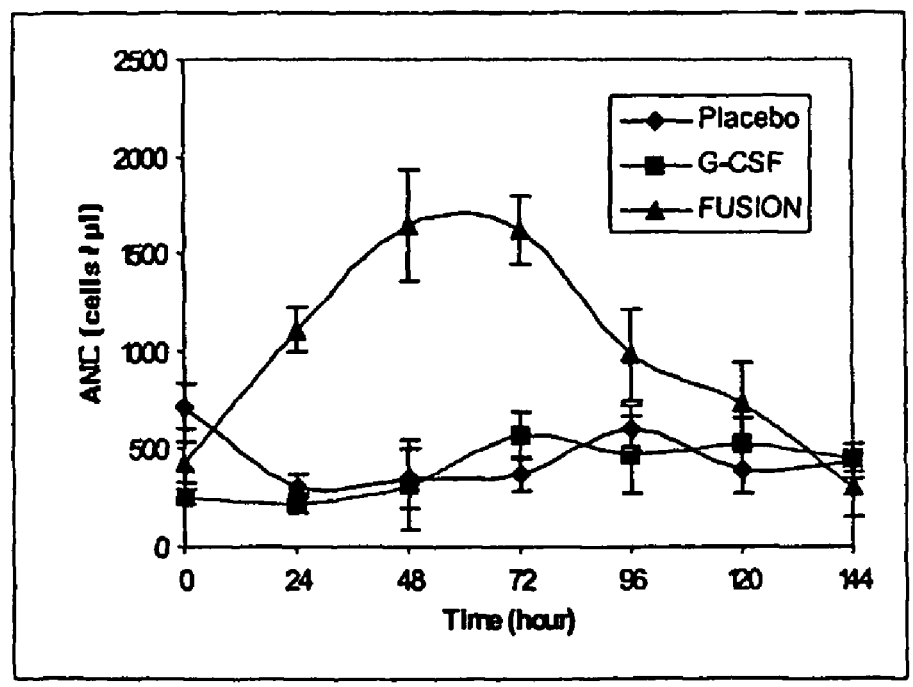
FIG. 12 shows myelopoietic effect of orally administered recombinant fusion protein, G-CSF, or control. G-CSF-Tf fusion protein or G-CSF was administered orally to BDF1 mice by gavage needle at doses of 50 or 10 mg/kg, respectively. Error bar represents SEM (n=3 for control and G-CSF, n=4 for fusion protein).
Figure 13:
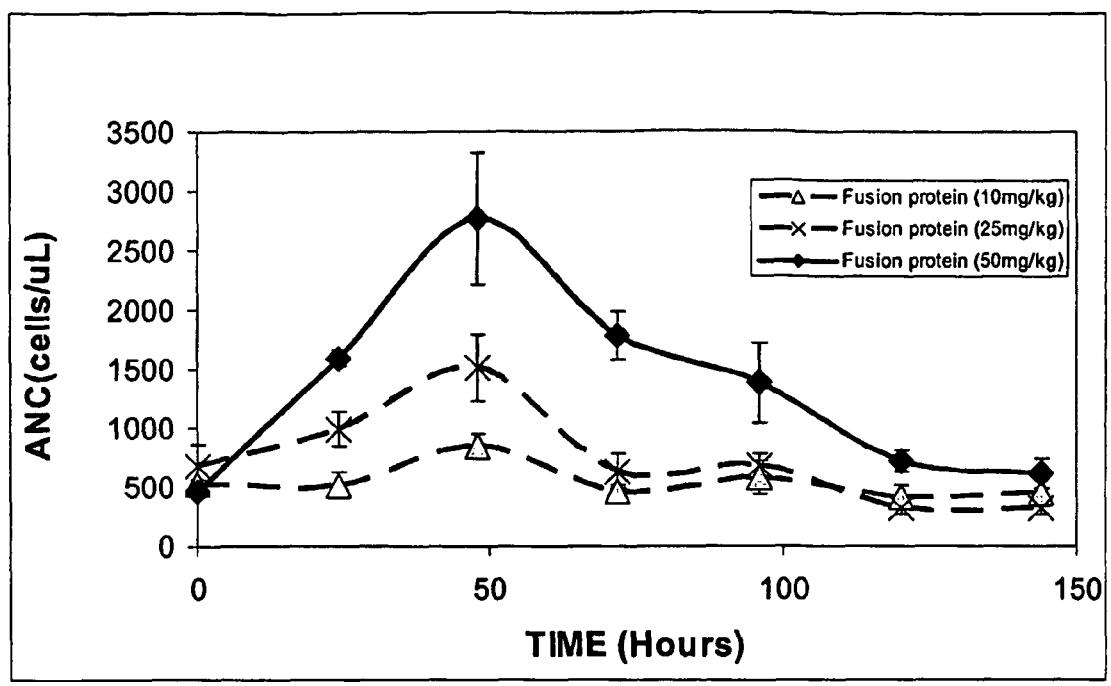
FIG. 13 shows dose-dependency of orally administered recombinant fusion protein. G-CSF-Tf fusion protein was administered orally to BDF1 mice by gavage needle at doses of 50 mg/kg, 25 mg/kg and 10 mg/kg. Myelopoietic effect was determined by daily absolute neutrophil counts. Error bar represent SEM (n=4).

For the oral delivery experiment, BDF1 mice were given 10 mg/kg filgrastim, 50 mg/kg fusion protein, or PBS control via a gavage needle. The mice that received fusion protein demonstrated a significant elevation in absolute neutrophil counts 24 hours post administration (1112±232 cells/µl versus 311±97 cells/µl in the control) (FIG. 12). In contrast, oral administration of filgrastim did not result in a statistically significant change in neutrophil level compared to control (219±85 cells/µl and 311±97 cells/ml for filgrastim and control groups after 24 hours, respectively). After 48 hours, the ANC of fusion protein group was further increased to 1643±575 cells/µl. The ANC of the fusion protein-treated group did not drop to base line until 120 hours post administration. Comparing the areas under the effective curve of G-CSF and the fusion protein in FIGS. 11 and 12, the bioequivalence of the orally administered fusion protein was estimated to be about 10% of the subcutaneously administered filgrastim or the fusion protein.

A dose response experiment was next performed on orally administered G-CSF-Tf fusion protein. BDF1 mice were given 50 mg/kg, 25 mg/kg; or 10 mg/kg fusion protein orally by gavage needle. Comparing the ANC on 48 hours, which is the peak point of the curve, they are 2769±962 cells/µl, 1512±566 cells/µl, 851±190 cells/µl, respectively. This result demonstrated that the myelopoietic effect of the fusion protein is dose-dependent.

Figure 14:
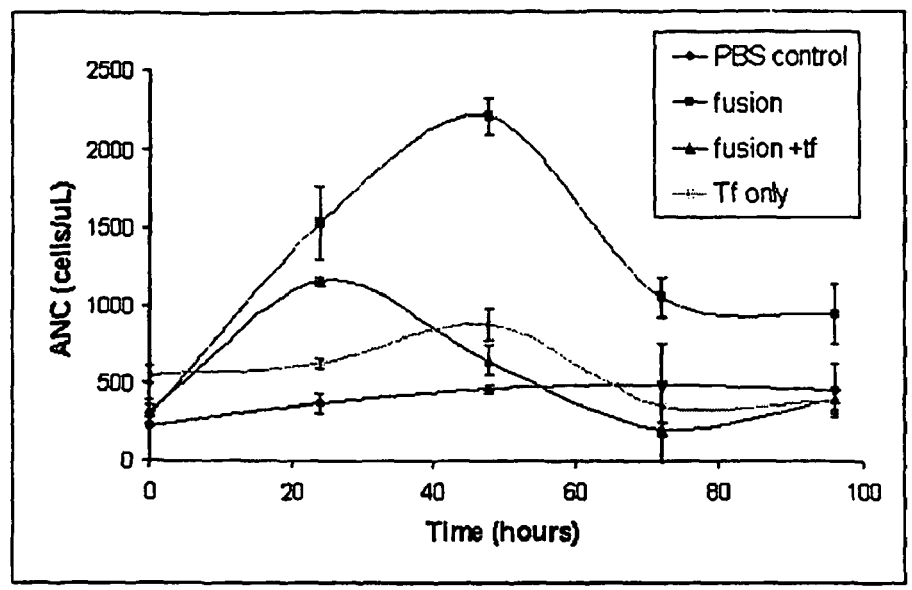
FIG. 14 shows competition of transferrin on the absorption of orally administered recombinant fusion protein. Fusion protein (50 mg/kg), fusion protein (50 mg/kg)+Tf (500 mg/kg), Tf (500 mg/kg) alone, and PBS as placebo were orally to BDF1 mice by gavage needle. Myelopoietic effect was determined by daily absolute neutrophil counts. Error bar represent SEM (n=3).
Figure 15:
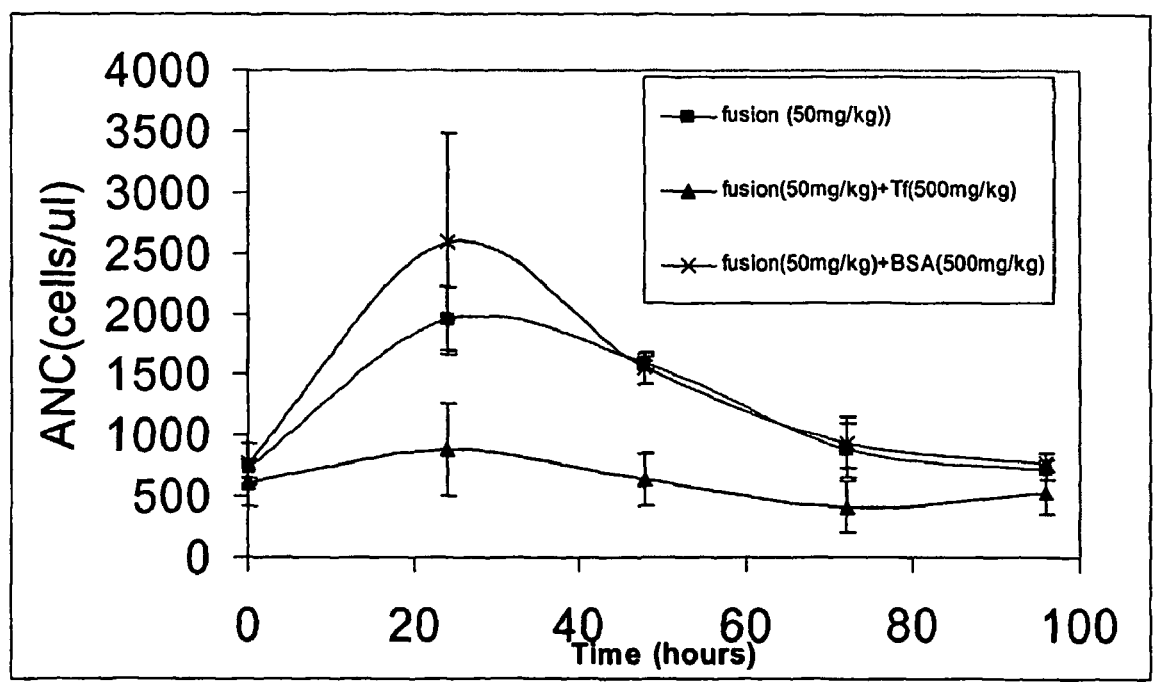
FIG. 15 shows effect of albumin on aborption of orally administered recombinant fusion protein. Fusion protein (50 mg/kg), fusion protein (50 mg/kg)+albumin (500 mg/kg), fusion protein (50 mg/kg)+transferrin (500 mg/kg) were orally to BDF1 mice via gavage needle. Myelopoietic effect was determined by daily absolute neutrophil counts.

To confirm that the fusion protein was transported across intestine epithelia into blood via a transferrin receptor-mediated pathway in vivo, we gave BDF1 mice fusion protein (50 mg/kg), or fusion protein (50 mg/kg) together with a 10-fold excess of transferrin (500 mg/kg). As showed in FIG. 14, there was a significant difference between the group treated with the fusion protein plus an excess of transferrin and the group treated with only the fusion protein. The difference was most striking at 48 hours when the ANC of the fusion protein-treated group increased to 2200±120 cells/µl, while the ANC of the group treated with the fusion protein with an excess of transferrin decreased to 642±100 cells/µl, which was not significantly different from the PBS control group. Furthermore, there was no significant different between the group treated with the fusion protein and the group treated with the fusion protein together with 500 mg/kg of bovine serum albumin (BSA) (FIG. 15). Therefore, the blockage of the fusion protein absorption by transferrin, but not by BSA, suggests that the oral absorption of the fusion protein is specific to the transferrin receptor.

While the foregoing has been described in considerable detail and in terms of preferred embodiments, these are not to be construed as limitations on the disclosure. Modifications and changes that are within the purview of those skilled in the art are intended to fall within the scope of the invention.

What is claimed is:

1. A fusion polypeptide comprising a granulocyte colony stimulating factor (G-CSF) domain operably linked to a transferrin (Tf) domain, wherein the ability of the polypeptide to be transported into a cell expressing a transferrin receptor (TfR) gene or the ability of the polypeptide to be transported across a cell expressing a TfR gene via transcytosis is higher than that of the G-CSF domain alone, wherein the polypeptide is a recombinant polypeptide, and wherein said Tf domain is preloaded with at least one iron molecule.

2. The fusion polypeptide of claim 1 further comprising a secretion signal at the N-terminus.

3. The fusion polypeptide of claim 1, wherein the G-CSF domain is N-terminus to the Tf domain.

4. A composition comprising a pharmaceutically acceptable carrier and the fusion polypeptide of claim 1 or 3.

5. The composition of claim 4, further comprising sodium bicarbonate, BSA, casein, or a combination thereof.

6. A method of enhancing production of circulating neutrophils in a subject, comprising administering to a subject in need thereof an effective amount of the composition of claim 4.

7. The method of claim 6, wherein the subject is undergoing chemotherapy for cancer, or is suffering from or at risk for developing severe chronic neutropenia or a bone marrow transplant-related disorder.

8. The method of claim 6, wherein the composition is administered orally.

9. The method of claim 6, wherein the composition is administered subcutaneously.

10. The fusion polypeptide of claim 1, wherein the Tf domain is preloaded with two iron molecules.

11. A method of enhancing transport of G-CSF into or across a gastrointestinal (GI) epithelial cell, comprising contacting the GI epithelial cell with the fusion polypeptide of claim 1 under conditions that allow transport of the fusion polypeptide into the cell through TfR or transport of the fusion polypeptide across the cell through TfR via transcytosis.

* * * * *